US006741877B1

(12) United States Patent
Shults et al.

(10) Patent No.: US 6,741,877 B1
(45) Date of Patent: *May 25, 2004

(54) DEVICE AND METHOD FOR DETERMINING ANALYTE LEVELS

(75) Inventors: Mark C. Shults, Madison, WI (US); Stuart J. Updike, Madison, WI (US); Rathbun K. Rhodes, Madison, WI (US)

(73) Assignee: DexCom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/489,588

(22) Filed: Jan. 21, 2000

Related U.S. Application Data

(60) Continuation of application No. 09/447,227, filed on Nov. 22, 1999, which is a division of application No. 08/811,473, filed on Mar. 4, 1997, now Pat. No. 6,001,067.

(51) Int. Cl.[7] ................................................. A61B 5/00
(52) U.S. Cl. ...................... 600/345; 600/347; 600/365; 600/573
(58) Field of Search ................................. 600/309, 345, 600/347, 365–366, 573, 582, 584; 424/422–425

(56) References Cited

U.S. PATENT DOCUMENTS

| | | | |
|---|---|---|---|
| 4,353,888 A | 10/1982 | Sefton | |
| 4,431,004 A | 2/1984 | Bessman et al. | |
| 4,436,094 A | 3/1984 | Cerami | |
| 4,484,987 A | 11/1984 | Gough | |
| 4,686,044 A | 8/1987 | Behnke et al. | |
| 4,703,756 A | 11/1987 | Gough et al. | |
| 4,757,022 A | 7/1988 | Shults et al. | |
| 4,759,828 A | 7/1988 | Young et al. | 204/1 T |
| 4,787,398 A | 11/1988 | Garcia et al. | |
| 4,803,243 A | 2/1989 | Fujimoto et al. | |

(List continued on next page.)

FOREIGN PATENT DOCUMENTS

| | | | |
|---|---|---|---|
| WO | WO 90/00738 | 1/1990 | |
| WO | WO 92/07525 | 5/1992 | |
| WO | WO 92/13271 | 8/1992 | |
| WO | WO 93/19701 | 10/1993 | A61F/2/02 |
| WO | WO 94/22357 | 10/1994 | |
| WO | WO 96/01611 | 1/1996 | |
| WO | WO 96/32076 | 10/1996 | |
| WO | WO 96/36296 | 11/1996 | |

OTHER PUBLICATIONS

Updkie et al., "Laboratory Evaluation of New Reusable Blood Glucose Sensor," *Diabetes Care,* 11:801–807 (1988).
Moatti–Sirat et al., "Towards Continuous Glucose Monitoring: In Vivo Evaluation of a Miniaturized Glucose Sensor Implanted for Several Days in Rate Subcutaneous Tissue," *Diabetologia* 35:224–30 (1992).

(List continued on next page.)

*Primary Examiner*—Robert L. Nasser
*Assistant Examiner*—Ryan Carter
(74) *Attorney, Agent, or Firm*—Knobbe Martens Olson & Bear LLP

(57) ABSTRACT

Devices and methods for determining analyte levels are described. The devices and methods allow for the implantation of analyte-monitoring devices, such as glucose monitoring devices, that result in the delivery of a dependable flow of blood to deliver sample to the implanted device. The devices comprise a unique microarchitectural arrangement in the sensor region that allows accurate data to be obtained over long periods of time.

320 Claims, 10 Drawing Sheets

U.S. PATENT DOCUMENTS

| | | | |
|---|---|---|---|
| 4,823,808 A | 4/1989 | Clegg et al. | |
| 4,890,620 A | 1/1990 | Gough | 128/635 |
| 4,902,294 A | 2/1990 | Gosserez | |
| 4,994,167 A | 2/1991 | Shults et al. | |
| 5,165,407 A | 11/1992 | Wilson et al. | 128/635 |
| 5,190,041 A * | 3/1993 | Palti | 600/347 |
| 5,314,471 A | 5/1994 | Brauker et al. | |
| 5,321,414 A | 6/1994 | Alden et al. | |
| 5,322,063 A | 6/1994 | Allen et al. | 128/635 |
| 5,344,454 A | 9/1994 | Clarkeet et al. | |
| 5,380,536 A | 1/1995 | Hubbell et al. | |
| 5,390,671 A | 2/1995 | Lord et al. | 128/635 |
| 5,391,250 A | 2/1995 | Cheney, II et al. | 156/268 |
| 5,417,395 A | 5/1995 | Fowler et al. | |
| 5,421,923 A | 6/1995 | Clarke et al. | |
| 5,431,160 A | 7/1995 | Wilkins | |
| 5,453,278 A | 9/1995 | Cham et al. | |
| 5,462,064 A | 10/1995 | D'Aneglo et al. | |
| 5,469,846 A | 11/1995 | Khan | |
| 5,476,094 A | 12/1995 | Allen et al. | |
| 5,497,772 A | 3/1996 | Schulman et al. | |
| 5,545,223 A | 8/1996 | Neuenfeldt et al. | |
| 5,549,675 A | 8/1996 | Neuenfeldt et al. | |
| 5,569,462 A | 10/1996 | Martinson et al. | |
| 5,578,463 A | 11/1996 | Berka et al. | |
| 5,593,440 A | 1/1997 | Brauker et al. | |
| 5,653,756 A | 8/1997 | Clarke et al. | |
| 5,660,163 A | 8/1997 | Schulman et al. | |
| 5,713,888 A | 2/1998 | Neuenfeldt et al. | |
| 5,733,336 A | 3/1998 | Neuenfeldt et al. | |
| 5,741,330 A * | 4/1998 | Brauker et al. | 623/11 |
| 5,777,060 A | 7/1998 | Van Antwerp | 528/28 |
| 5,782,912 A | 7/1998 | Brauker et al. | |
| 5,791,344 A * | 8/1998 | Schulman et al. | 600/347 |
| 5,800,529 A | 9/1998 | Brauker et al. | |
| 5,807,406 A | 9/1998 | Brauker et al. | |
| 5,882,354 A | 3/1999 | Brauker et al. | |
| 5,882,494 A | 3/1999 | Van Antwerp | 204/403 |
| 5,964,261 A | 10/1999 | Neuefeldt et al. | |
| 6,001,067 A * | 12/1999 | Shults et al. | 600/584 |
| 6,122,536 A | 9/2000 | Sun et al. | |
| 6,208,894 B1 | 3/2001 | Schulman et al. | |
| 6,212,416 B1 | 4/2001 | Ward et al. | |
| 6,256,522 B1 | 7/2001 | Schultz | |
| 6,259,937 B1 | 7/2001 | Schulman et al. | |
| 6,309,351 B1 | 10/2001 | Kurnik et al. | 600/309 |
| 6,329,161 B1 | 12/2001 | Heller et al. | 435/14 |
| 6,400,974 B1 * | 6/2002 | Lesho | 600/347 |

OTHER PUBLICATIONS

Armour et al., "Application of Chronic Intravascular Blood Glucose Sensor in Dogs," *Diabetes* 39:1519–26 (1990).

Woodward, "How Fibroblasts and Giant Cells Encapsulate Implants: Considerations in Design of Glucose Sensor," *Diabetes Care* 5:278–281 (1982).

Bindra et al., "Design and In Vitro Studies of a Needle–Type Glucose Sensor for Subcutaneous Monitoring," *Anal. Chem.* 63:1692–96 (1991).

Shults et al., A Telemetry–Instrumentation System for Monitoring Multiple Subcutaneously Impaired Glucose Sensors, *IEEE Trans, Biomed. Eng.* 41:937–942 (1994).

Philips and Smith, "Biomedical Applications of Polyurethanes: Implications of Failure Mechanisms," *J. Biomat. Appl.* 3:202–227 (1988).

Stokes, "Polyether Polyurethanes: Biostable or Not?," *J. Biomat. Appl.* 3:228–259 (1988).

Updike et al. Enzymatic Glucose Sensors: Improved Long–Term Performance In Vitro and In Vivo, *Am.Soc. Artificial Internal Organs* 40:157–163 (1994).

Updike et al., Implanting the Glucose Enzyme Electrode: Problems, Progress, and Alternative Solutions, *Diabetes Care* 5:207–21 (1982).

Rhodes et al., "Prediction of Pocket–Portable and Implantable Glucose Enzyme Electrode Performance from Combined Species Permeability and Digital Simulation Analysis," *Anal. Chem.* 66:1520–1529 (1994).

Tse and Gough, Time–Dependent Inactivation of Immobilized Glucose Oxidase and Catalase, *Biotechnol. Bioeng.* 29:705–713 (1987).

Gilligan et al., "Evaluation of a Subcutaneous Glucose Sensor Out to 3 Months in a Dog Model," *Diabetes Care* 17:882–887 (1994).

McKean and Gough, "A Telemetry–Instrumentation System for Chronically Implanted Glucose and Oxygen Sensors," *IEEE Trans. Biomed. Eng.* 35:526–532 (1988).

Shichiri et al., "Telemetry Glucose Monitoring Device with Needle–Type Glucose Sensor–A Useful Tool for Blood Glucose Monitoring in Diabetic Individuals," *Diabetes Care* 9:298–301 (1986).

Lyman, "Polyurethanes. I. The Solution Polymerization of Diisocyanates with Ethylene Glycol," *J. Polymer. Sci.* 45:49 (1960).

DuPont[1] Dimension AR® (Catalog).

Direct 30/30® meter (Markwell Medical) (Catalog).

Fischer et al., "Oxygen Tension at the Subcutaneous Implantation Site of Glucose Sensors," *Biomed. Biochem.* 11/12, 965–972 (1989).

Brauker et al., "Neovascularization of Synthetic Membranes Directed by Membrane Microarchitecture," *Journal of Biomedical Materials Research* 29:1517 (1995).

Abstract presented by James Brauker, Ph.D., "Neovascularization of Cell Transplantation Devices: Membrane Architecture–Driven and Implanted Tissue–Driven Vascularization," Baxter Healthcare Corp.

Brauker et al., "Local Inflammatory Response Around Diffusion Chambers Containing Xenografts", Transplantation, vol. 61, 1671–1677, No. 12, Jun. 27, 1996.

* cited by examiner

DEVICE AND METHOD FOR DETERMINING ANALYTE LEVELS

This is a Continuation of U.S. patent application Ser. No. 09/447,227 filed on Nov. 22, 1999, which is a Divisional of U.S. patent application Ser. No. 08/811,473 filed on Mar. 4, 1997, which issued on Dec. 14, 1999 as U.S. Pat. No. 6,001,067.

FIELD OF THE INVENTION

The present invention relates generally to devices and methods for determining analyte levels, and, more particularly, to implantable devices and methods for monitoring glucose levels in a biological fluid.

BACKGROUND OF THE INVENTION

The continuous measurement of substances in biological fluids is of interest in the control and study of metabolic disorders. Electrode systems have been developed for this purpose whereby an enzyme-catalyzed reaction is monitored (e.g., by the changing concentrations of reactants or products) by an electrochemical sensor. In such electrode systems, the electrochemical sensor comprises an electrode with potentiometric or amperometric function in close contact with a thin layer containing an enzyme in dissolved or insoluble form. Generally, a semipermeable membrane separates the thin layer of the electrode containing the enzyme from the sample of biological fluid that includes the substance to be measured.

Electrode systems that include enzymes have been used to convert amperometrically inactive substances into reaction products which are amperometrically active. For example, in the analysis of blood for glucose content, glucose (which is relatively inactive amperometrically) may be catalytically converted by the enzyme glucose oxidase in the presence of oxygen and water to gluconic acid and hydrogen peroxide. Tracking the concentration of glucose is possible since for every glucose molecule converted a proportional change in either oxygen or hydrogen peroxide sensor current will occur [U.S. Pat. Nos. 4,757,022 and 4,994,167 to Shults et al., both of which are hereby incorporated by reference]. Hydrogen peroxide is anodically active and produces a current which is proportional to the concentration of hydrogen peroxide, which is directly related to the concentration of glucose in the sample. [Updike et al., Diabetes Care, 11:801–807 (1988)].

Despite recent advances in the field of implantable glucose monitoring devices, presently used devices are unable to provide data safely and reliably for long periods of time (e.g., months or years) [See, e.g., Moatti-Sirat et al., Diabetologia 35:224–30 (1992)]. For example, Armour et al., Diabetes 39:1519–26 (1990), describes a miniaturized sensor that is placed intravascularly, thereby allowing the tip of the sensor to be in continuous contact with the blood. Unfortunately, probes that are placed directly into the vasculature put the recipient at risk for thrombophlebosis, thromboembolism, and thrombophlebitis.

Currently available glucose monitoring devices that may be implanted in tissue (e.g., subcutaneously) are also associated with several shortcomings. For example, there is no dependable flow of blood to deliver sample to the tip of the probe of the implanted device. Similarly, in order to be effective, the probe must consume some oxygen and glucose, but not enough to perturb the available glucose which it is intended to measure; subcutaneously implanted probes often reside in a relatively stagnant environment in which oxygen or glucose depletion zones around the probe tip may result in erroneously low measured glucose levels. Finally, the probe may be subject to "motion artifact" because the device is not adequately secured to the tissue, thus contributing to unreliable results. Partly because of these limitations, it has previously been difficult to obtain accurate information regarding the changes in the amounts of analytes (e.g., whether blood glucose levels are increasing or decreasing); this information is often extremely important, for example, in ascertaining whether immediate corrective action is needed in the treatment of diabetic patients.

There is a need for a device that accurately and continuously determines the presence and the amounts of a particular analyte, such as glucose, in biological fluids. The device should be easy to use, be capable of accurate measurement of the analyte over long periods of time, and should not readily be susceptible to motion artifact.

SUMMARY OF THE INVENTION

The present invention relates generally to devices and methods for determining analyte levels, and, more particularly, to implantable devices and methods for monitoring glucose levels in a biological fluid.

The devices and methods of the present invention allow for the implantation of analyte-monitoring devices such as glucose monitoring devices that result in a dependable flow of blood to deliver sample to the implanted device at a concentration representative of that in the vasculature. Moreover, the devices of the present invention become secured within the tissue of the subject, thereby greatly reducing or eliminating the phenomenon of "motion artifact". In addition, the devices of the present invention utilize materials that eliminate or significantly delay environmental stress cracking at the sensor interface, resulting in the ability to obtain accurate, long-term data.

These effects result, in part, from the use of materials that enhance the formation of a foreign body capsule (FBC). Previously, FBC formation has been viewed as being adverse to sensor function, and researchers have attempted to minimize FBC formation (see, e.g., U.S. Pat. No. 5,380,536 to Hubbell et al.). However, the methods and devices of the present invention utilize specific materials and microarchitecture that elicit a type of FBC that does not hamper the generation of reliable data for long periods. The devices of the present invention are capable of accurate operation in the approximately 37° C., low $pO_2$, environment characteristic of living tissue for extended lengths of time (e.g., months to years).

The electrode-membrane region of the devices of the present invention comprises a unique microarchitectural arrangement. In preferred embodiments, the electrode surfaces are in contact with (or operably connected with) a thin electrolyte phase, which in turn is covered by an enzyme membrane that contains an enzyme, e.g., glucose oxidase, and a polymer system. A bioprotective membrane covers this enzyme membrane system and serves, in part, to protect the sensor from external forces and factors that may result in environmental stress cracking. Finally, an angiogenic layer is placed over the bioprotective membrane and serves to promote vascularization in the sensor interface region. It is to be understood that other configurations (e.g., variations of that described above) are contemplated by the present invention and are within the scope thereof.

The present invention contemplates a biological fluid measuring device, comprising a) a housing comprising electronic circuit means and at least two electrodes operably connected to the electronic circuit means; and b) a sensor means operably connected to the electrodes of the housing, the sensor means comprising i) a bioprotective membrane, and ii) an angiogenic layer, the angiogenic layer positioned more distal to the housing than the bioprotective membrane. In particular embodiments, the bioprotective membrane is substantially impermeable to macrophages. In some embodiments, the bioprotective membrane comprises pores having diameters ranging from about 0.1 micron to about 1.0 micron. In certain embodiments, the bioprotective membrane comprises polytetrafluoroethylene, and in particular embodiments, the angiogenic layer also comprises polytetrafluoroethylene.

Particular embodiments of the biological fluid measuring device further comprise c) means for securing the device to biological tissue, the securing means associated with the housing. In some embodiments, the securing means comprises a polyester velour jacket. In preferred embodiments, the securing means covers the top surface (e.g., the top member or the top member sheath, as described further below) and a portion of the sensor interface; it should be noted that the securing means generally should not cover the entire sensor interface, as this would interfere with the ability of blood vessels to deliver sample to the biological fluid measuring device. In preferred embodiments, the securing means comprises poly(ethylene terephthalate).

In further embodiments, the sensor means of the biological fluid measuring device further comprises means for determining the amount of glucose in a biological sample. In some embodiments, the glucose determining means comprises a membrane containing glucose oxidase, the glucose oxidase-containing membrane positioned more proximal to the housing than the bioprotective membrane. In additional embodiments, the housing further comprises means for transmitting data to a location external to the device (e.g., a radiotelemetry device).

The present invention also contemplates a device for measuring glucose in a biological fluid, comprising a) a housing comprising electronic circuit means and at least one electrode operably connected to the electronic circuit means; and b) a sensor means operably connected to the electrode of the housing, the sensor means comprising i) means for determining the amount of glucose in a biological sample, the glucose determining means operably associated with the electrode, ii) a bioprotective membrane, the bioprotective membrane positioned more distal to the housing than the glucose determining means and substantially impermeable to macrophages, and iii) an angiogenic layer, the angiogenic layer positioned more distal to the housing than the bioprotective membrane.

In particular embodiments, the glucose determining means comprises a membrane containing glucose oxidase. In some embodiments, the angiogenic layer comprises polytetrafluoroethylene.

In some embodiments, the pores of the bioprotective membrane have diameters ranging from about 0.1 micron to about 1.0 micron, while in other embodiments the pores have diameters ranging from about 0.2 micron to about 0.5 micron. In certain embodiments, the bioprotective membrane comprises polytetrafluoroethylene.

Still other embodiments further comprise c) means for securing the device to biological tissue, the securing means associated with the housing. In particular embodiments, the securing means comprises poly(ethylene terephthalate). Additional embodiments comprise means for transmitting data to a location external to the device; in some embodiments, the data transmitting means comprises a radiotelemetric device.

The present invention also contemplates a method for monitoring glucose levels, comprising a) providing i) a host, and ii) a device comprising a housing and means for determining the amount of glucose in a biological fluid; and b) implanting the device in the host under conditions such that the device measures the glucose accurately for a period exceeding 90 days. In some embodiments, the device measures glucose accurately for a period exceeding 150 days, while in other embodiments, the device measures glucose accurately for a period exceeding 360 days.

The present invention also contemplates a method of measuring glucose in a biological fluid, comprising a) providing i) a host, and ii) a device comprising a housing and means for determining the amount of glucose in a biological fluid, the glucose determining means capable of accurate continuous glucose sensing; and b) implanting the device in the host under conditions such that the continuous glucose sensing begins between approximately day 2 and approximately day 25. In some embodiments, the continuous glucose sensing begins between approximately day 3 and approximately day 21. In particular embodiments, the implanting is subcutaneous.

The devices of the present invention allow continuous information regarding, for example, glucose levels. Such continuous information enables the determination of trends in glucose levels, which can be extremely important in the management of diabetic patients.

DEFINITIONS

In order to facilitate an understanding of the present invention, a number of terms are defined below.

The term "accurately" means, for example, 95% of measured values within 25% of the actual value as determined by analysis of blood plasma, preferably within 15% of the actual value, and most preferably within 5% of the actual value. It is understood that like any analytical device, calibration, calibration check and recalibration are required for the most accurate operation of the device.

The term "analyte" refers to a substance or chemical constituent in a biological fluid (e.g., blood or urine) that can be analyzed. A preferred analyte for measurement by the devices and methods of the present invention is glucose.

The terms "sensor interface," "sensor means," and the like refer to the region of a monitoring device responsible for the detection of a particular analyte. For example, in some embodiments of a glucose monitoring device, the sensor interface refers to that region wherein a biological sample (e.g., blood or interstitial fluid) or a portion thereof contacts (directly or after passage through one or more membranes or layers) an enzyme (e.g., glucose oxidase); the reaction of the biological sample (or portion thereof) results in the formation of reaction products that allow a determination of the glucose level in the biological sample. In preferred embodiments of the present invention, the sensor means comprises an angiogenic layer, a bioprotective layer, an enzyme layer, and an electrolyte phase (i.e., a free-flowing liquid phase comprising an electrolyte-containing fluid [described further below]). In some preferred embodiments, the sensor interface protrudes beyond the plane of the housing.

The terms "operably connected," "operably linked," and the like refer to one or more components being linked to another component(s) in a manner that allows transmission of, e.g., signals between the components. For example, one or more electrodes may be used to detect the amount of analyte in a sample and convert that information into a signal; the signal may then be transmitted to electronic circuit means (i.e., the electrode is "operably linked" to the electronic circuit means), which may convert the signal into a numerical value in the form of known standard values.

The term "electronic circuit means" refers to the electronic circuitry components of a biological fluid measuring device required to process information obtained by a sensor means regarding a particular analyte in a biological fluid, thereby providing data regarding the amount of that analyte in the fluid. U.S. Pat. No. 4,757,022 to Shults et al., previously incorporated by reference, describes suitable electronic circuit means (see, e.g., FIG. 7); of course, the present invention is not limited to use with the electronic circuit means described therein. A variety of circuits are contemplated, including but not limited to those circuits described in U.S. Pat. Nos. 5,497,772 and 4,787,398, hereby incorporated by reference.

The terms "angiogenic layer," "angiogenic membrane," and the like refer to a region, membrane, etc. of a biological fluid measuring device that promotes and maintains the development of blood vessels microcirculation around the sensor region of the device. As described in detail below, the angiogenic layer of the devices of the present invention may be constructed of membrane materials alone or in combination such as polytetrafluoroethylene, hydrophilic polyvinylidene fluoride, mixed cellulose esters, polyvinyl chloride, and other polymers including, but not limited to, polypropylene, polysulphone, and polymethacrylate.

The phrase "positioned more distal" refers to the spatial relationship between various elements in comparison to a particular point of reference. For example, some embodiments of a biological fluid measuring device comprise both a bioprotective membrane and an angiogenic layer/membrane. If the housing of the biological fluid measuring device is deemed to be the point of reference and the angiogenic layer is positioned more distal to the housing than the bioprotective layer, then the bioprotective layer is closer to the housing than the angiogenic layer.

The terms "bioprotective membrane," "bioprotective layer," and the like refer to a semipermeable membrane comprised of protective biomaterials of a few microns thickness or more which are permeable to oxygen and glucose and are placed over the tip of the sensor to keep the white blood cells (e.g., tissue macrophages) from gaining proximity to and then damaging the enzyme membrane. In some embodiments, the bioprotective membrane has pores (typically from approximately 0.1 to approximately 1.0 micron). In preferred embodiments, a bioprotective membrane comprises polytetrafluoroethylene and contains pores of approximately 0.4 microns in diameter. Pore size is defined as the pore size provided by the manufacturer or supplier.

The phrase "substantially impermeable to macrophages" means that few, if any, macrophages are able to cross a barrier (e.g., the bioprotective membrane). In preferred embodiments, fewer than 1% of the macrophages that come in contact with the bioprotective membrane are able to cross.

The phrase "means for securing said device to biological tissue" refers to materials suitable for attaching the devices of the present invention to, e.g., the fibrous tissue of a foreign body capsule. Suitable materials include, but are not limited to, poly(ethylene terephthalate). In preferred embodiments, the top of the housing is covered with the materials in the form of surgical grade fabrics; more preferred embodiments also contain material in the sensor interface region (see FIG. 1B).

The phrase "means for determining the amount of glucose in a biological sample" refers broadly to any mechanism (e.g., enzymatic or non-enzymatic) by which glucose can be quantitated. For example, some embodiments of the present invention utilize a membrane that contains glucose oxidase that catalyzes the conversion of glucose to gluconate: Glucose+$O_2$→Gluconate+$H_2O_2$. Because for each glucose molecule converted to gluconate, there is a proportional change in the co-reactant $O_2$ and the product $H_2O_2$, one can monitor the current change in either the co-reactant or the product to determine glucose concentration.

The phrase "means for transmitting data to a location external to said device" refers broadly to any mechanism by which data collected by a biological fluid measuring device implanted within a subject may be transferred to a location external to the subject. In preferred embodiments of the present invention, radiotelemetry is used to provide data regarding blood glucose levels, trends, and the like. The terms "radiotelemetry," "radiotelemetric device," and the like refer to the transmission by radio waves of the data recorded by the implanted device to an ex vivo recording station (e.g., a computer), where the data is recorded and, if desired, further processed (see, e.g., U.S. Pat. Nos. 5,321,414 and 4,823,808, hereby incorporated by reference; PCT Pat. Publication WO 9422367).

The term "host" refers to both humans and animals.

The phrase "continuous glucose sensing" refers to the period in which monitoring of plasma glucose concentration is continuously carried out. More specifically, at the beginning of the period in which continuous glucose sensing is effected, the background sensor output noise disappears, and the sensor output stabilizes (e.g., over several days) to a long-term level reflecting adequate microcirculatory delivery of glucose and oxygen to the tip of the sensor (see FIG. 2). Though an understanding of this effect is not required in order to practice the present invention, it is believed to be due to adequately vascularized foreign body capsule tissue in consistent contact with the sensor interface of the blood glucose monitoring device. Failure of adequate vascularization or consistent contact of tissue with sensor will result in failure of continuous glucose sensing.

DESCRIPTION OF THE INVENTION

Figure 1A:
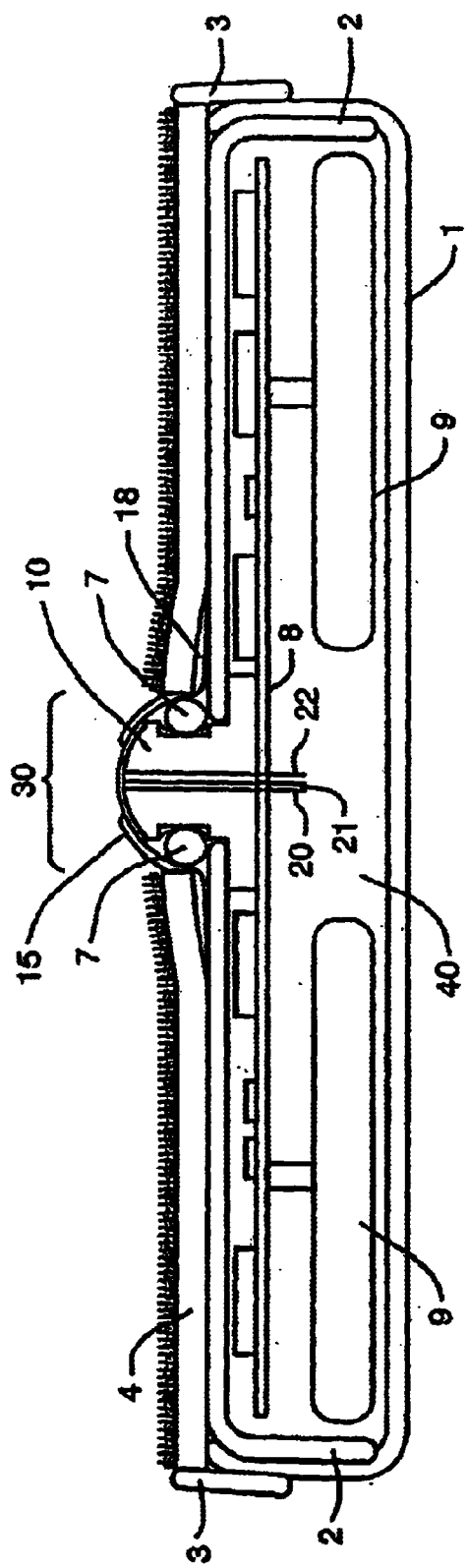
FIG. 1A depicts a cross-sectional drawing of one embodiment of an implantable analyte measuring device of the present invention.

The present invention relates generally to devices and methods for determining analyte levels, and, more particularly, to implantable devices and methods for monitoring glucose levels in a biological fluid. In a preferred embodiment, the device and methods of the present invention are used to determine the level of glucose in a subject, a particularly important measurement for individuals having diabetes.

Although the description that follows is primarily directed at glucose monitoring devices and methods for their use, the devices and methods of the present invention are not limited to glucose measurement. Rather, the devices and methods may be applied to detect and quantitate other analytes present in biological fluids (including, but not limited to, amino acids and lactate), especially those analytes that are substrates for oxidase enzymes [see, e.g., U.S. Pat. No. 4,703,756 to Gough et al., hereby incorporated by reference]. Moreover, the devices and methods of the present invention may be utilized to present components of biological fluids to measurement methods which are not enzyme-based, including, but not limited to, those based on surface plasmon resonance, surface acoustic waves, optical absorbance in the long wave infrared region, and optical rotation of polarized light.

I. Nature of the Foreign Body Capsule

Probes that are implanted (e.g., subcutaneously) into tissue will almost always elicit a foreign body capsule (FBC) as part of the body's response to the introduction of a foreign material. Though a precise understanding of the nature of a FBC is not required in order to practice the present invention, generally speaking, upon implantation of a glucose sensor, there is initially an acute inflammatory reaction (which includes invasion of tissue macrophages), followed by building of fibrotic tissue. A mature capsule (i.e., the FBC) comprising primarily avascular fibrous tissue forms around the device [Woodward, Diabetes Care, 5:278–281 (1982)]. Although fluid is frequently found within the capsular space between the sensor and the capsule, levels of analytes (e.g., glucose and oxygen) within the fluid often do not mimic levels in the body's vasculature, making accurate measurement difficult. Example 4 below describes typically identifiable phases in FBC formation as reflected by response of an implanted glucose sensor.

In general, the formation of FBCs has precluded the collection of reliable, continuous information because they isolate the sensor of the implanted device from biological fluids, fully equilibrated with at least the low molecular weight components found in the circulation. Similarly, the composition of FBCs has prevented stabilization of the implanted device, contributing to motion artifact that renders unreliable results. Thus, conventionally, it has been the practice of those skilled in the art to attempt to minimize FBC formation by, for example, using a short lived needle geometry or sensor coatings to minimize the foreign body reaction.

In contrast to the prior art, the teachings of the present invention recognize that FBC formation is the dominant event surrounding long term implantation of any sensor and must be orchestrated to support rather than hinder or block sensor performance. For example, sensors often do not perform well until the FBC has matured sufficiently to provide ingrowth of well attached tissue bearing a rich supply of capillaries directly to the surface of the sensor. This maturation process takes at least several days and, when initiated according to the present invention, is a function of biomaterial and host factors which initiate and modulate angiogenesis, and promote and control fibrocyte ingrowth. The present invention contemplates the use of particular materials to promote angiogenesis adjacent to the sensor interface (also referred to as the electrode-membrane region, described below) and to anchor the device within the FBC.

II. The Implantable Glucose Monitoring Devices of the Present Invention

The present invention contemplates the use of a unique microarchitectural organization around the sensor interface of an implantable device. Moreover, the present invention contemplates the use of materials covering all or a portion of the device to assist in the stabilization of the device following implantation. However, it should be pointed out that the present invention does not require a device comprising particular electronic components (e.g., electrodes, circuitry, etc). Indeed, the teachings of the present invention can be used with virtually any monitoring device suitable for implantation (or subject to modification allowing implantation); suitable devices include, but are not limited, to those described in U.S. Pat. Nos. 4,703,756 and 4,994,167 to Shults et al.; U.S. Pat. No. 4,703,756 to Gough et al., and U.S. Pat. No. 4,431,004 to Bessman et al.; the contents of each being hereby incorporated by reference, and Bindra et al., Anal. Chem. 63:1692–96 (1991).

In the discussion that follows, an example of an implantable device that includes the features of the present invention is first described. Thereafter, the specific characteristics of, for example, the sensor interface contemplated by the present invention will be described in detail.

Generally speaking, the implantable devices contemplated for use with the present invention are oval shaped; of course, devices with other shapes may also be used with the present invention. The sample device includes a housing having an upper portion and a lower portion which together define a cavity. FIG. 1A depicts a cross-sectional drawing of one embodiment of an implantable measuring device. Referring to FIG. 1A, the device comprises a main housing (also referred to as casing or packaging) consisting of a bottom member 1 with upwardly angled projecting extensions along its perimeter. The four downwardly projecting extensions of a similarly-shaped top member 2 engage the upwardly projecting extensions of the bottom member 1. As indicated in FIG. 1A, there is an aperture in top member 2 that allows for protrusion of the sensor interface dome 30. Preferred embodiments of the present invention entail such a protrusion of the sensor interface dome 30; in some embodiments, though a precise understanding of the effect of the protrusion is not required in order to practice the present invention, the protrusion is believed to assist in the formation of vasculature in the sensor interface dome 30 region, and hence presentation of sample to the electrodes.

In certain embodiments, a top member sheath 4 covers the top member 2; like the top member 2, the top member sheath 4 has an aperture which allows the sensor interface dome 30 to protrude therethrough. As indicated in detail in FIG. 1B, the top member sheath 4 angles upward as it approaches the aperture, allowing the sensor interface capsular attachment layer 15 to be secured thereto. The top member sheath 4 may be coated with a sheath capsular attachment layer 16; in some embodiments, the sheath capsular attachment layer extends beyond the top member sheath (e.g., it may jacket the sides of the device or the bottom member).

Maintaining the blood supply near an implanted foreign body like an implanted analyte-monitoring sensor requires stable fixation of FBC tissue on the surface of the foreign body. This can be achieved, for example, by using capsular attachment membrane materials (e.g., those materials that comprise the sensor interface and top member capsular attachment layers) developed to repair or reinforce tissues, including, but not limited to, polyester (DACRON®; DuPont; poly(ethylene terephthalate)) velour, expanded polytetrafluoroethylene (TEFLON®; Gore), polytetrafluoroethylene felts, polypropylene cloth, and related porous implant materials. The preferred material for FBC attachment is surgical-grade polyester velour. FBC tissue tends to aggressively grow into the materials disclosed above and form a strong mechanical bond (i.e., capsular attachment); this fixation of the implant in its capsule is essential to prevent motion artifact or disturbance of the newly-developed capillary blood supply. In preferred embodiments, capsular attachment materials are not used in the region of the sensor interface so as not to interfere with the vasculature development in that region.

Side braces 3 secure the top member sheath 4 to the bottom member 1 (see FIG. 1A). A conventional O-ring 7 or other suitable mechanical means may be used to assist in the attachment of the membrane layers (e.g., the enzyme layer). In a preferred embodiment, the housing is approximately 1.4 cm from the base of the bottom member 1 to the top of the sheath capsular attachment layer 16, and approximately 7.0 cm in length.

The interior (i.e., the cavity) of the housing comprises one or more batteries 9 operably connected to an electronic circuit means (e.g., a circuit board 8), which, in turn, is operably connected to at least one electrode (described below); in preferred embodiments, at least two electrodes are carried by the housing. Any electronic circuitry and batteries that renders reliable, continuous, long-term (e.g., months to years) results may be used in conjunction with the devices of the present invention.

The housing of the devices of the present invention preferably utilize a simple, low-cost packaging technique which protects the components of the device for at least one year in aqueous media. In preferred embodiments, the components of the housing (e.g., the top and bottom members) comprise thermoformed high-density polyethylene. The area in the cavity of the housing that surrounds the batteries, electronic circuitry, etc., may be filled with an encapsulant 40 (see FIG. 1A), a material that secures in place the components within the cavity but that does not interfere with the operation of those components. In preferred embodiments, the encapsulant 40 is based on mixtures of petroleum wax and low melting temperature resins developed for the hot-melt glue industry [Shults et al., IEEE Trans. Biomed. Eng. 41:937–942 (1994)]. In addition to the high-quality moisture barrier formed with this approach, the electronics (e.g., the circuit board 8) can be recycled by remelting and draining the encapsulant when the battery expires.

The preferred encapsulant compositions of the present invention comprise approximately 54% PW 130/35H wax (Astor Wax), approximately 40% MVO 2528 resin (Exxon Chemical), and approximately 6% XS 93.04 resin (Exxon Chemical, Houston, Tex.). These pelletized compounds render a well-mixed solution after heating and mixing at about 120° C. for approximately one hour. This solution is then poured into the polyethylene housing containing the implant electronics, taking caution to not to exceed the burst temperature of, e.g., approximately 160° C. when lithium batteries are used.

Figure 1B:
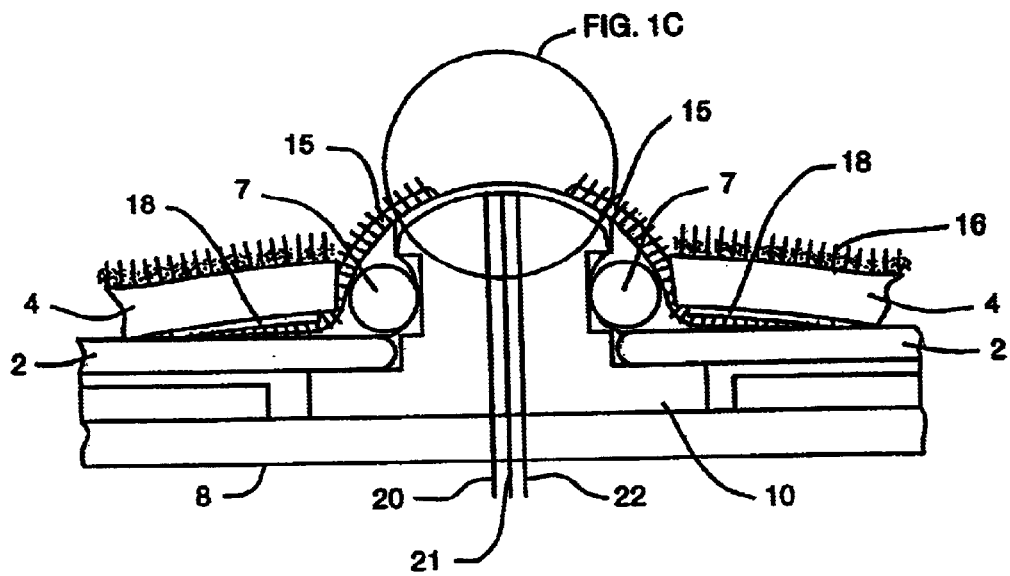
FIG. 1B depicts a cross-sectional exploded view of the sensor interface dome of FIG. 1A.

FIG. 1B depicts a cross-sectional exploded view of the sensor interface dome 30 of FIG. 1A. Referring to FIG. 1B, the sensor interface dome comprises a region of, for example, epoxy insulation 10 in which is embedded a silver reference electrode 20, a platinum working electrode 21, and a platinum counter electrode 22. The present invention is neither limited by the composition of the electrodes nor their position within the sensor interface dome 30.

Figure 1C:
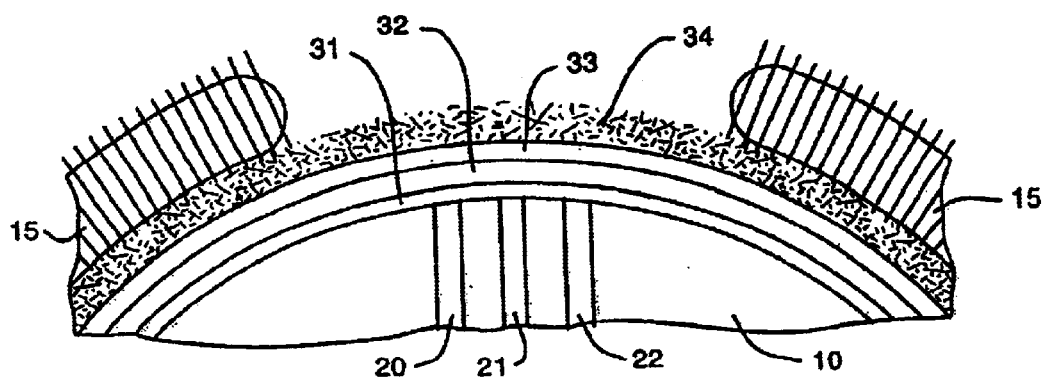
FIG. 1C depicts across-sectional exploded view of the electrode-membrane region of FIG. 1B detailing the sensor tip and the functional membrane layers.

FIG. 1C depicts a cross-sectional exploded view of the electrode-membrane region set forth in FIG. 1B detailing the sensor tip and the functional membrane layers. As depicted in FIG. 1C, the electrode-membrane region comprises several different membrane layers, the compositions and functions of which are described in detail below. The top ends of the electrodes are in contact with the electrolyte phase 31, a free-flowing fluid phase. The electrolyte phase is covered by the enzyme membrane 32 that contains an enzyme, e.g., glucose oxidase, and several functional polymer layers (as described below). In turn, a bioprotective membrane 33 covers the enzyme membrane 32 and serves, in part, to protect the sensor from external forces that may result in environmental stress cracking of the enzyme membrane 32. Finally, an angiogenic layer 34 is placed over the bioprotective membrane 33 and serves to promote vascularization in the sensor interface region.

A retaining gasket 18 composed of, for example, silicone rubber, is used to retain the sensor interface capsular attachment layer 15 (FIGS. 1A–B) and the angiogenic layer 34 and the bioprotective membrane 33 (not shown). In preferred embodiments, the angiogenic layer 34 and the bioprotective membrane 33 pass over the tip of the sensor interface dome 30, over the O-ring 7, and then under the sensor interface capsular attachment layer 15 and the retaining gasket 18.

The present invention contemplates the construction of the membrane layers of the sensor interface region using standard film coating techniques. This type of membrane fabrication facilitates control of membrane properties and membrane testing.

III. Sensor Interface

As alluded to above and disclosed in FIG. 1C, in a preferred embodiment, the sensor interface region comprises several different layers and membranes that cover the electrodes of an implantable analyte-measuring device. The characteristics of these layers and membranes are now discussed in more detail. The layers and membranes prevent direct contact of the biological fluid sample with the electrodes, while permitting selected substances (e.g., analytes) of the fluid to pass therethrough for electrochemical reaction with the electrodes.

The membranes used in the sensor interface region are semipermeable membranes. Generally speaking, the two fundamental diffusion processes by which a semipermeable membrane can limit the amount of a substance that passes therethrough are i) diffusion through the semipermeable membrane as a porous structure and ii) diffusion through the semipermeable membrane as a monolithic, homogeneous structure. The present invention is not limited by the nature of the semipermeable membranes used in the sensor interface region.

A semipermeable membrane that comprises a porous structure consists of a relatively impermeable matrix that includes a plurality of "microholes" or pores of molecular dimensions. Transfer through these membranes is primarily due to passage of substances through the pores (i.e., the membrane acts as a microporous barrier or sieve). Examples of materials that may be used to form porous, semipermeable membranes include, but are not limited to, polyethylene, polyvinylchloride, polytetrafluoroethylene, polypropylene, polyacrylamide, cellulose acetate, polymethyl methacrylate, silicone polymers, polycarbonate, and cellulosic polymers.

Because diffusion is primarily due to passage of the substance through pores, the permeability is related to the effective size of the pores, the membrane thickness, and to the molecular size of the diffusing substance. As a result, there is little selectivity in the separation of two chemically or structurally related molecules, except when their molecular size is approximately the same as the size of the pore; when this occurs, forces acting between the substance and the surface of the pore channel may influence the rate of transfer. In addition, the upper size limit to diffusion is determined by the largest pore diameter, and the overall diffusion rate depends on the total number of pores.

In contrast, passage of a substance through a monolithic, homogeneous membrane depends upon selective dissolution and diffusion of the substance as a solute through a solid, non-porous film. As used herein, the term "monolithic" means substantially non-porous and having a generally unbroken surface. The term "homogeneous", with reference to a membrane, means having substantially uniform characteristics from one side of the membrane to the other. However, a membrane may have heterogeneous structural domains, for example, created by using block copolymers (i.e., polymers in which different blocks of identical monomer units alternate with each other), and still be characterized functionally as homogeneous with respect to its dependence upon dissolution rather than sieving to effect separation of substances. A monolithic membrane can thus be used to selectively separate components of a solution on the basis of properties other than the size, shape and density of the diffusing substances. Monolithic, homogeneous membranes act as a barrier because of the preferential diffusion therethrough of some substance. They may be formed from materials such as those previously listed for porous membranes, including, but not limited to, polyethylene, polyvinylchloride, tetrafluorethylene, polypropylene, polyacrylamide, polymethyl methacrylate, silicone polymers, polycarbonate, collagen, polyurethanes and block copolymers thereof (block copolymers are discussed in U.S. Pat. Nos. 4,803,243 and 4,686,044, hereby incorporated by reference).

A. Angiogenic Layer

For implantable glucose monitoring devices, a sensor/tissue interface must be created which provides the sensor with oxygen and glucose concentrations comparable to that normally available to tissue comprised of living cells. Absent such an interface, the sensor is associated with unstable and chaotic performance indicating that inadequate oxygen and/or glucose are reaching the sensor. The development of suitable interfaces in other contexts has been reported. For example, investigators have developed techniques which stimulate and maintain blood vessels inside a FBC to provide for the demanding oxygen needs of pancreatic islets within an implanted membrane. [See, e.g., Brauker et al., Abstract from 4th World Biomaterials Congress, Berlin (1992)]. These techniques depend, in part, on the use of a vascularizing layer on the exterior of the implanted membrane. However, previously-described implantable analyte-monitoring devices have not been able to successfully maintain sufficient blood flow to the sensor interface.

As described above, the outermost layer of the electrode-membrane region comprises an angiogenic material. The angiogenic layer of the devices of the present invention may be constructed of membrane materials such as hydrophilic polyvinylidene fluoride (e.g., Durapore®; Millipore), mixed cellulose esters (e.g., MF; Millipore), polyvinyl chloride (e.g., PVC; Millipore), and other polymers including, but not limited to, polypropylene, polysulphone, and polymethacrylate. Preferably, the thickness of the angiogenic layer is about 10 $\mu$m to about 20 $\mu$m. The angiogenic layer comprises pores sizes of about 0.5 to about 20 $\mu$m, and more preferably about 1.0 $\mu$m to about 10 $\mu$m, sizes that allow most substances to pass through, including, e.g., macrophages. The preferred material is expanded PTFE of a thickness of about 15 $\mu$m and pore sizes of about 5 $\mu$m to about 10 $\mu$m.

To further promote stable foreign body capsule structure without interfering with angiogenesis, an additional outermost layer of material comprised of a thin low-density non-woven polyester (e.g., manufactured by Gore) can be laminated over the preferred PTFE described above. In preferred embodiments, the thickness of this layer is about 120 $\mu$m. This additional thin layer of material does not interfere with angiogenesis and enhances the manufacturability of the angiogenic layer. [See U.S. Pat. No. 5,453,278 to Brauker et al., hereby incorporated by reference; PCT Pat. Publication Nos. 96/32076, 96/01611, and 92/07525 assigned to Baxter].

B. Bioprotective Membrane

The inflammatory response that initiates and sustains a FBC is associated with both advantages and disadvantages. Some inflammatory response is needed to create a new capillary bed in close proximity to the surface of the sensor in order to i) continuously deliver adequate oxygen and glucose and ii) create sufficient tissue ingrowth to anchor the implant and prevent motion artifact. On the other hand, inflammation is associated with invasion of tissue macrophages which have the ability to biodegrade many artificial biomaterials (some of which were, until recently, considered nonbiodegradable). When activated by a foreign body, tissue macrophages degranulate, releasing from their cytoplasmic myeloperoxidase system hypochlorite (bleach), $H_2O_2$ and other oxidant species. Both hypochlorite and $H_2O_2$ are known to break down a variety of polymers, including polyurethane, by a phenomenon referred to as environmental stress cracking. [Phillips et al., J. Biomat. Appl., 3:202–227 (1988); Stokes, J. Biomat. Appl. 3:228–259 (1988)]. Indeed, environmental stress cracking has been shown to limit the lifetime and performance of an enzyme-active polyurethane membrane stretched over the tip of a glucose sensor. [Updike et al., Am. Soc. Artificial Internal Organs, 40:157–163 (1994)].

Because both hypochlorite and $H_2O_2$ are short-lived chemical species in vivo, biodegradation will not occur if macrophages are kept a sufficient distance from the enzyme active membrane. The present invention contemplates the use of protective biomaterials of a few microns thickness or more (i.e., a bioprotective membrane) which are permeable to oxygen and glucose and are placed over the tip of the sensor to keep the macrophages from gaining proximity to the sensor membrane. The devices of the present invention are not limited by the nature of the bioprotective layer. However, the bioprotective layer should be biostable for long periods of time (e.g., several years); the present invention contemplates the use of polymers including, but not limited to, polypropylene, polysulphone, polytetrafluoroethylene (PTFE), and poly(ethylene terephthalate) (PET).

Preferably, the bioprotective layer is constructed of expanded PTFE with a pore size of about 0.2 μm to about 0.5 μm and a thickness of about 15 to about 35 μm. Most preferably, the bioprotective layer is constructed of expanded PTFE with a pore size of 0.4 μm and a thickness of approximately 25 μm (e.g., Millicell CM-Biopore®; Millipore).

C. The Enzyme Membrane

Figure 1D:
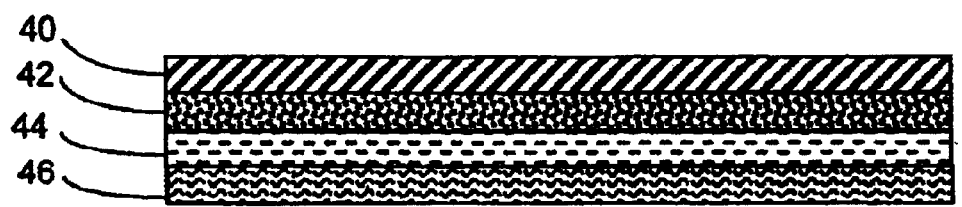
FIG. 1D depicts an enzyme layer including a resistance layer, an enzyme layer, an interface layer, and an electrolyte layer (layers not to scale).

The present invention contemplates membranes impregnated with enzyme. It is not intended that the present invention be limited by the nature of the enzyme membrane. The enzyme membrane of a preferred embodiment is depicted in FIG. 1C as being a single, homogeneous structure. However, in preferred embodiments, the enzyme membrane comprises a plurality of distinct layers. In a particularly preferred embodiment, as depicted in FIG. 1D, the enzyme membrane comprises the following four layers (in succession from the bioprotective membrane to the electrolyte phase): i) a resistance layer 40; ii) an enzyme layer 42; iii) an interference layer 44; and iv) an electrolyte layer 46.

Resistance Layer

There is a molar excess of glucose relative to the amount of oxygen in samples of blood. Indeed, for every free oxygen molecule in extracellular fluid, there are typically more than 100 glucose molecules present [Updike et al., Diabetes Care 5:207–21(1982)]. However, an immobilized enzyme-based sensor using oxygen ($O_2$) as cofactor must be supplied with oxygen in non-rate-limiting excess in order to respond linearly to changes in glucose concentration while not responding to changes in oxygen tension. More specifically, when a glucose-monitoring reaction is oxygen-limited, linearity is not achieved above minimal concentrations of glucose. Without a semipermeable membrane over the enzyme layer, linear response to glucose levels can be obtained only up to about 40 mg/dL; however, in a clinical setting, linear response to glucose levels are desirable up to at least about 500 mg/dL.

The resistance layer comprises a semipermeable membrane that controls the flux of oxygen and glucose to the underlying enzyme layer (i.e., limits the flux of glucose), rendering the necessary supply of oxygen in non-rate-limiting excess. As a result, the upper limit of linearity of glucose measurement is extended to a much higher value than that which could be achieved without the resistance layer. The devices of the present invention contemplate resistance layers comprising polymer membranes with oxygen-to-glucose permeability ratios of approximately 200:1; as a result, one-dimensional reactant diffusion is adequate to provide excess oxygen at all reasonable glucose and oxygen concentrations found in the subcutaneous matrix [Rhodes et al., Anal. Chem., 66:1520–1529 (1994)].

In preferred embodiments, the resistance layer has a thickness of less than about 45 μm, more preferably in the range of about 15 to about 40 μm and most preferably in the range of about 20 to about 35 μm.

Enzyme Layer

In addition to glucose oxidase, the present invention contemplates the use of a membrane layer impregnated with other oxidases, e.g., galactose oxidase, uricase. For an enzyme-based electrochemical glucose sensor to perform well, the sensor's response must neither be limited by enzyme activity nor cofactor concentration. Because enzymes, including the very robust glucose oxidase, are subject to deactivation as a function of ambient conditions, this behavior needs to be accounted for in constructing sensors for long-term use.

The principle of losing half of the original enzyme activity in a specific time may be used in calculating how much enzyme needs to be included in the enzyme layer to provide a sensor of required lifetime (see Experimental section). Previously, researchers have found that, when placed in a saline solution at 37° C., glucose electrodes lose half of their electrode enzyme activity in 85 to 105 days [See, e.g., Tse and Gough, Biotechnol. Bioeng. 29:705–713 (1987)]. Under reasonable diabetic conditions and normal enzyme loading (e.g., $2 \times 10^{-4}$ M glucose oxidase; see Example 4), useful sensor lifetimes can last for at least one year. However, exposure of the sensor to high levels of glucose in combination with low oxygen levels for prolonged periods can result in shortened sensor lifetimes. [Rhodes et al., Anal. Chem., 66:1520–1529 (1994)].

Excess glucose oxidase loading is required for long sensor life. The Experimental section provides a procedure that can be used to determine the appropriate amount of enzyme to be included in the enzyme layer. When excess glucose oxidase is used, up to two years of performance is possible from the glucose-monitoring devices contemplated by the present invention.

Interference Layer

The interference layer comprises a thin, hydrophobic membrane that is non-swellable and has a low molecular weight cut-off. The interference layer is permeable to relatively low molecular weight substances, such as hydrogen peroxide, but restricts the passage of higher molecular weight substances, including glucose and ascorbic acid. The interference layer serves to allow analytes and other substances that are to be measured by the electrodes to pass through, while preventing passage of other substances.

The interference layer has a preferred thickness of less than about 5 μm, more preferably in the range of about 0.1 to about 5 μm and most preferably in the range of about 0.5 to about 3 μm.

Electrolyte Layer

To ensure electrochemical reaction, the electrolyte layer comprises a semipermeable coating that maintains hydrophilicity at the electrode region of the sensor interface. The electrolyte layer enhances the stability of the interference layer of the present invention by protecting and supporting the membrane that makes up the interference layer. Furthermore, the electrolyte layer assists in stabilizing operation of the device by overcoming electrode start-up problems and drifting problems caused by inadequate electrolyte. The buffered electrolyte solution contained in the electrolyte layer also protects against pH-mediated damage that may result from the formation of a large pH gradient between the hydrophobic interference layer and the electrode (or electrodes) due to the electrochemical activity of the electrode.

Preferably the coating comprises a flexible, water-swellable, substantially solid gel-like film having a "dry film" thickness of about 2.5 μm to about 12.5 μm, preferably about 6.0 μm. "Dry film" thickness refers to the thickness of a cured film cast from a coating formulation onto the surface of the membrane by standard coating techniques. The coating formulation comprises a premix of film-forming polymers and a crosslinking agent and is curable upon the application of moderate heat.

Suitable coatings are formed of a curable copolymer of a urethane polymer and a hydrophilic film-forming polymer.

Particularly preferred coatings are formed of a polyurethane polymer having anionic carboxylate functional groups and non-ionic hydrophilic polyether segments, which is crosslinked in the present of polyvinylpyrrolidone and cured at a moderate temperature of about 50° C.

Particularly suitable for this purpose are aqueous dispersions of fully-reacted colloidal polyurethane polymers having cross-linkable carboxyl functionality (e.g., BAYBOND®; Mobay Corporation). These polymers are supplied in dispersion grades having a polycarbonate-polyurethane backbone containing carboxylate groups identified as XW-121 and XW-123; and a polyester-polyurethane backbone containing carboxylate groups, identified as XW-110-2. Particularly preferred is BAYBOND® 123, an aqueous anionic dispersion of an aliphate polycarbonate urethane polymer sold as a 35 weight percent solution in water and co-solvent N-methyl-2-pyrrolidone.

Polyvinylpyrrolidone is also particularly preferred as a hydrophilic water-soluble polymer and is available commercially in a range of viscosity grades and average molecular weights ranging from about 18,000 to about 500,000, under the PVP K® homopolymer series by BASF Wyandotte and by GAF Corporation. Particularly preferred is the homopolymer having an average molecular weight of about 360,000 identified as PVP-K90 (BASF Wyandotte). Also suitable are hydrophilic, film-forming copolymers of N-vinylpyrrolidone, such as a copolymer of N-vinylpyrrolidone and vinyl acetate, a copolymer of N-vinylpyrrolidone, ethylmethacrylate and methacrylic acid monomers, and the like.

The polyurethane polymer is crosslinked in the presence of the polyvinylpyrrolidone by preparing a premix of the polymers and adding a cross-linking agent just prior to the production of the membrane. Suitable cross-linking agents can be carboduimides, epoxides and melamine/formaldehyde resins. Carboduimide is preferred, and a preferred carbodiimide crosslinker is UCARLNK® XL-25 (Union Carbide).

The flexibility and hardness of the coating can be varied as desired by varying the dry weight solids of the components in the coating formulation. The term "dry weight solids" refers to the dry weight percent based on the total coating composition after the time the crosslinker is included. A preferred useful coating formulation can contain about 6 to about 20 dry weight percent, preferably about 8 dry weight percent, polyvinylpyrrolidone; about 3 to about 10 dry weight percent preferably about 5 dry weight percent cross-linking agent; and about 70 to about 91 weight percent, preferably about 87 weight percent of a polyurethane polymer, preferably a polycarbonate-polyurethane polymer. The reaction product of such a coating formulation is referred to herein as a water-swellable cross-linked matrix of polyurethane and polyvinylpyrrolidone.

D. The Electrolyte Phase

The electrolyte phase is a free-fluid phase comprising a solution containing at least one compound, usually a soluble chloride salt, that conducts electric current. The electrolyte phase flows over the electrodes (see FIG. 1C) and is in contact with the electrolyte layer of the enzyme membrane. The devices of the present invention contemplate the use of any suitable electrolyte solution, including standard, commercially available solutions.

Generally speaking, the electrolyte phase should have the same or less osmotic pressure than the sample being analyzed. In preferred embodiments of the present invention, the electrolyte phase comprises normal saline.

E. Electrode

The electrode assembly of this invention may also be used in the manner commonly employed in the making of amperometric measurements. A sample of the fluid being analyzed is placed in contact with a reference electrode, e.g., silver/silver-chloride, and the electrode of this invention which is preferably formed of platinum. The electrodes are connected to a galvanometer or polarographic instrument and the current is read or recorded upon application of the desired D.C. bias voltage between the electrodes.

The ability of the present device electrode assembly to accurately measure the concentration of substances such as glucose over a broad range of concentrations in fluids including undiluted whole blood samples enables the rapid and accurate determination of the concentration of those substances. That information can be employed in the study and control of metabolic disorders including diabetes.

IV. Sensor Implantation and Radiotelemetric Output

Long-term sensor performance is best achieved, and transcutaneous bacterial infection is eliminated, with implanted devices capable of radiotelemetric output. The present invention contemplates the use of radiotelemetry to provide data regarding blood glucose levels, trends, and the like. The term "radiotelemetry" refers to the transmission by radio waves of the data recorded by the implanted device to an ex vivo recording station (e.g., a computer), where the data is recorded and, if desired, further processed.

Although totally implanted glucose sensors of three month lifetime, with radiotelemetric output, have been tested in animal models at intravenous sites [see, e.g. Armour et al., Diabetes, 39:1519–1526 (1990)], subcutaneous implantation is the preferred mode of implantation [see, e.g., Gilligan et al., Diabetes Care 17:882–887 (1994)]. The subcutaneous site has the advantage of lowering the risk for thrombophlebitis with hematogenous spread of infection and also lowers the risk of venous thrombosis with pulmonary embolism. In addition, subcutaneous placement is technically easier and more cost-effective than intravenous placement, as it may be performed under local anesthesia by a non-surgeon health care provider in an outpatient setting.

Preferably, the radiotelemetry devices contemplated for use in conjunction with the present invention possess features including small package size, adequate battery life, acceptable noise-free transmission range, freedom from electrical interference, and easy data collection and processing. Radiotelemetry provides several advantages, one of the most important of which is the ability of an implanted device to measure analyte levels in a sealed-off, sterile environment.

The present invention is not limited by the nature of the radiotelemetry equipment or methods for its use. Indeed, commercially available equipment can be modified for use with the devices of the present invention (e.g., devices manufactured by Data Sciences). Similarly, custom-designed radiotelemetry devices like those reported in the literature can be used in conjunction with the implantable analyte-measuring devices of the present invention [see, e.g., McKean and Gough, IEEE Trans. Biomed. Eng. 35:526–532 (1988); Shichiri et al., Diabetes Care 9:298–301 (1986); and Shults et al., IEEE Trans. Biomed. Eng. 41:937–942 (1994)]. In a preferred embodiment, transmitters are programmed with an external magnet to transmit at 4-, 32-, or 256-second intervals depending on the need of the subject; presently, battery lifetimes at the current longest transmission intervals (about 256 seconds) is approximately up to two years.

V. Response Time and Calibration

Every measurement method reports data with some delay after the measured event. For data to be useful, this delay must be smaller than some time depending on the needs of the method. Thus, response time of the current invention has been carefully studied. The use of the term "initial response" is not to be confused with the term "response time." After a step function change in glucose concentration, the time delay before the first unequivocal change in sensor signal occurs is the "initial response," while the following time delay to reach 90% of the steady-state signal development is the "response time." "Response time" is the factor which normally controls how quickly a sensor can track a dynamically changing system.

Furthermore, the time required before a glucose sensor in a FBC will indicate an initial response to a bolus intravenous glucose injection is a function of the animal "circulation time" and the sensor's "initial response". The circulation time is the time required for a bolus glucose injection to reach the site of sensor implantation.

Generally speaking, equilibration between vascular and interstitial compartments for glucose is so rapid that it plays no role in either the initial response or the observed response time. If the tip of the sensor is in intimate contact with the interstitial compartment (e.g., FBC), then there is no significant delay in glucose diffusing from the capillary lumen to the tip of the sensor. The inventors have found that the glucose sensors of the present invention provide initial responses of about 30 seconds in dogs about half of which is circulation time. The dog model represents a useful and accepted model for determining the efficacy of glucose monitoring devices.

While the devices of the present invention do not require a specific response time, in preferred embodiments of the present invention, the in vitro 90% response times at 37° C. for subsequently subcutaneously implanted devices are in the range of 2 to 5 minutes in dogs. Though the use of the devices of the present invention does not require an understanding of the factors that influence response time or the factors' mechanisms of action, in vivo response times are believed to be primarily a function of glucose diffusion through the sensor membrane (e.g., a 40–60 micron membrane). Of note, response times of up to about 10 minutes do not limit the clinical utility of tracking blood glucose in diabetic patients because physiologic or pathologic glucose levels do not change more rapidly than a few percent per minute.

In calibrating the glucose sensors of the present invention, a single point recalibration of the sensor at four-week intervals against an acceptable glucose reference method is preferred (e.g., calibration against blood obtained from a finger-prick). Generally speaking, the recalibration amounts to a simple adjustment in sensor gain. The sensor offset current (i.e., the current at 0 mg/dL glucose) needs to remain invariant over the duration of the implant for the sensor to provide optimal data.

Experimental

The following examples serve to illustrate certain preferred embodiments and aspects of the present invention and are not to be construed as limiting the scope thereof.

In the preceding description and the experimental disclosure which follows, the following abbreviations apply: Eq and Eqs (equivalents); mEq (milliequivalents); M (molar); mM (millimolar) $\mu$M (micromolar); N (Normal); mol (moles); mmol (millimoles); $\mu$mol (micromoles); nmol (nanomoles); g (grams); mg (milligrams); $\mu$g (micrograms); Kg (kilograms); L (liters); mL (milliliters); dL (deciliters); $\mu$L (microliters); cm (centimeters); mm (millimeters); $\mu$m (micrometers); nm (nanometers); h and hr (hours); min. (minutes); s and sec. (seconds); °C. (degrees Centigrade); Astor Wax (Titusville, Pa.); BASF Wyandotte Corporation (Parsippany, N.J.); Data Sciences, Inc. (St. Paul, Minn.); DuPont (DuPont Co., Wilmington, Del.); Exxon Chemical (Houston, Tex.); GAF Corporation (New York, N.Y.); Markwell Medical (Racine, Wis.); Meadox Medical, Inc. (Oakland, N.J.); Mobay (Mobay Corporation, Pittsburgh, Pa.); Sandoz (East Hanover, N.J.); and Union Carbide (Union Carbide Corporation; Chicago, Ill.).

EXAMPLE 1

The polyurethanes are preferably prepared as block copolymers by solution polymerization techniques as generally described in Lyman [J. Polymer Sci. 45:49 (1960)]. Specifically, a two-step solution polymerization technique is used in which the poly(oxyethylene)glycol is first "capped" by reaction with a diisocyanate to form a macrodiusocyanate. The macrodiisocyanate is then coupled with a diol (or diamine) and the diisocyanate to form a block copolyetherurethane (or a block copolyurethaneurea). The resulting block copolymers are tough and elastic and may be solution-cast in N,N-dimethylformamide to yield clear films that demonstrate good wet strength when swollen in water.

In particular, a mixture of 8.4 g (0.006 mol), poly (oxyethylene)glycol (CARBOWAX® 1540, Union Carbide), and 3.0 g (0.012 mol) 4,4'-diphenylmethane diusocyanate in 20 mL dimethyl sulfoxide/4-methyl-2-pentanone (50/50) is placed in a three-necked flask equipped with a stirrer and condenser and protected from moisture. The reaction mixture is stirred and heated at 110° C. for about one hour. To this clear solution is added 1.5 g (0.014 mol) 1,5-pentanediol and 2.0 g (0.008 mol) 4,4'-diphenylmethane diisocyanate.

After heating at 110° C. for an additional two hours, the resulting viscous solution is poured into water. The tough, rubbery, white polymer precipitate that forms is chopped in a Waring Blender, washed with water and dried in a vacuum oven at about 60° C. The yield is essentially quantitative. The inherent viscosity of the copolymer in N,N-dimethyl formamide is 0.59 at 30° C. (at a concentration of about 0.05 percent by weight).

EXAMPLE 2

As previously described, the electrolyte layer, the membrane layer closest to the electrode, can be coated as a water-swellable film. This example illustrates a coating comprising a polyurethane having anionic carboxylate functional groups and hydrophilic polyether groups and polyvinylpyrrolidone (PVP) that can be cross-linked by carbodiimide.

A coating preparation is prepared comprising a premix of a colloidal aqueous dispersion of particles of a urethane polymer having a polycarbonate-polyurethane (PC-PU) backbone containing carboxylate groups and the water-soluble hydrophilic polymer, PVP, which is crosslinked by the addition of the cross-linking agent just before production of the coated membrane. Example coating formulations are illustrated in Table 1.

TABLE 1

|  | A | | B | | C | |
|---|---|---|---|---|---|---|
|  | Weight | Dry Weight % Solids | Weight | Dry Weight % Solids | Weight | Dry Weight % Solids |
| Premix |  |  |  |  |  |  |
| PVP[1] | 48 | 6 | 64 | 8 | 160 | 20 |
| PC-PV[2] | 260 | 91 | 248 | 87 | 200 | 70 |
| Cross-Linking Agent |  |  |  |  |  |  |
| Carbodiimide[3] | 6 | 3 | 10 | 5 | 20 | 10 |
| Totals | 314 | 100 | 322 | 100 | 380 | 100 |

[1] Aqueous solution containing 12.5 weight percent PVP prepared from polyvinylpyrrolidone having a number average molecular weight of about 360,000 sold as a powder under the trademark BASF K90 by BASF Wyandotte Corporation.
[2] Colloidal dispersion of a polycarbonatepolyurethane (PCPU) polymer at about 35 weight percent solids in a co-solvent mixture of about 53 weight percent water and about 12 weight percent N-methyl-2-pyrrolidone (BAYBOND ® 123 or XW123; Mobay Corporation). As supplied, the dispersion has a pH of about 7.5–9.0.
[3] Carbodiimide (UCARLNK ® XL25SE, Union Carbide Corporation) supplied at about 50 weight percent solids in a solvent solution of propylene glycol monomethylether acetate.

The viscosity and pH of the premix can be controlled and maintained during processing and to prolong its useful life by adding water or adjusting the pH with dilute ammonia solution or an equivalent base prior to adding the crosslinker.

For production, the coating is applied with a Mayer rod onto the unbound surface of a multilayered membrane. The amount of coating applied should cast a film having a "dry film" thickness of about 2.5 μm to about 12.5 μm, preferably about 6.0 μm. The coating is dried above room temperature preferably at about 50° C. This coating dries to a substantially solid gel-like film that is water swellable to maintain electrolyte between the membrane covering the electrode and the electrode in the electrode assembly during use.

EXAMPLE 3

The following procedure was used to determine the amount of enzyme to be included in the enzyme layer. It is to be understood that the present invention is not limited to the use of this or a similar procedure, but rather contemplates the use of other techniques known in the art.

A starting glucose oxidase concentration of $2 \times 10^{-4}$ M was calculated from the enzyme weight and the final volume of the enzyme layer. Thereafter, a series of eight additional membrane formulations was prepared by decrementing enzyme concentration in 50% steps (referred to as a change of one "half loading") down to $7.8 \times 10^{-7}$ M. Sensor responses were then collected for this range of enzyme loadings and compared to computer-simulated sensor outputs. The simulation parameter set used included previously-determined membrane permeabilities and the literature mechanisms and kinetics for glucose oxidase. [Rhodes et al., Anal. Chem., 66:1520–1529 (1994)].

There was a good match of real-to-simulated sensor output at all loadings (data not shown). Approximately a six-to-seven "half loading" drop in enzyme activity was required before the sensor output dropped 10%; another two-to-three half loading drop in enzyme activity was required to drop the sensor response to 50% of the fully loaded sensor response. These results indicate that, at the loading used and the decay rates measured, up to two years of performance is possible from these sensors when the sensor does not see extended periods of high glucose and physiologically low $O_2$ concentrations.

EXAMPLE 4

This example illustrates long-term glucose sensor device response following subcutaneous implantation of sensor devices contemplated by the present invention into a dog. The stages of FBC development are indicated by the long term glucose sensor device response.

Figure 2:
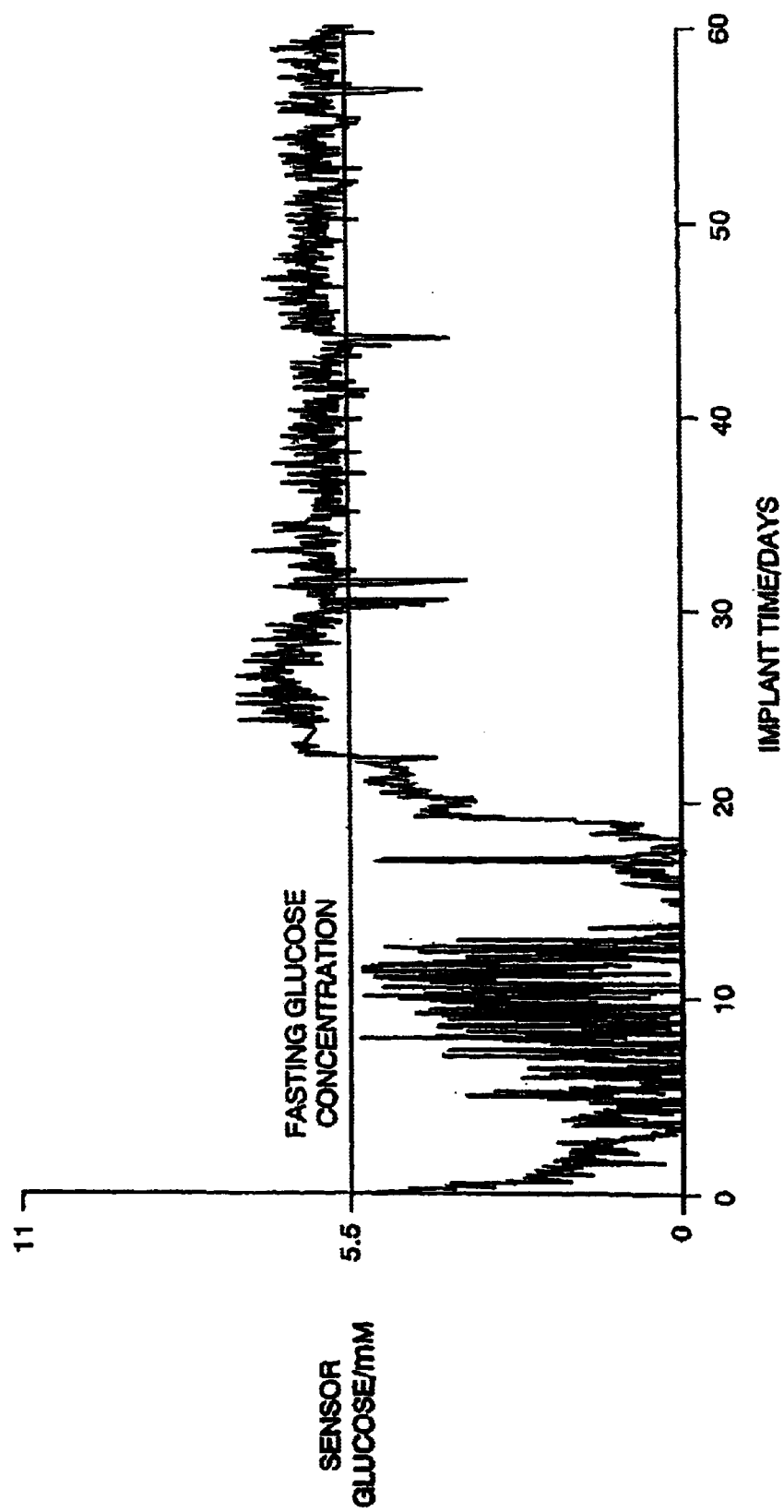
FIG. 2 graphically depicts glucose levels as a function of the number of days post-implant.

FIG. 2 graphically depicts glucose levels as a function of the number of days post-implant. The data in FIG. 2 was taken at four-minute intervals for 60 days after implantation. Sensor response is calculated from a single preimplant calibration at 37° C. Normal canine fasting glucose concentration of 5.5 mM is shown for comparison.

The data set forth in FIG. 2 can be used to illustrate the four typically identifiable phases in FBC formation. Phase 1 shows rapidly dropping response from the time of implant to, in this case, day 3. Though an understanding of the mechanism for this drop in sensor output is not required in order to practice the present invention, it is believed to reflect low $pO_2$ and low glucose present in fluid contacting the sensor. Phase 2 shows intermittent sensor-tissue contact in seroma fluid from, in this case, day 3 to about day 13. During this phase, fragile new tissue and blood supply intermittently make contact with the sensor (which is surrounded by seroma fluid). Phase 3 shows stabilization of capillary supply between, in this case, days 13 and 22. More specifically, the noise disappears and sensor output rises over approximately six days to a long term level associated with tracking of FBC glucose. Again, though an understanding of this effect is not required to practice the present invention, the effect is believed to reflect consistent contact of FBC tissue with the sensor surface. Phase 4 from, in this case, day 22 to day 60, shows duration of useful sensor device life. While there are timing variations of the stages from sensor device to sensor device, generally speaking, the first three steps of this process take from 3 days to three weeks and continuous sensing has been observed for periods thereafter (e.g., for periods of 150 days and beyond).

EXAMPLE 5

In addition to collecting normoglycemic or non-diabetic dog data from the sensor of the present invention as shown in Example 4, calibration stability, dynamic range, freedom from oxygen dependence, response time and linearity of the sensor can be studied by artificial manipulation of the intravenous glucose of the sensor host.

Figure 3:
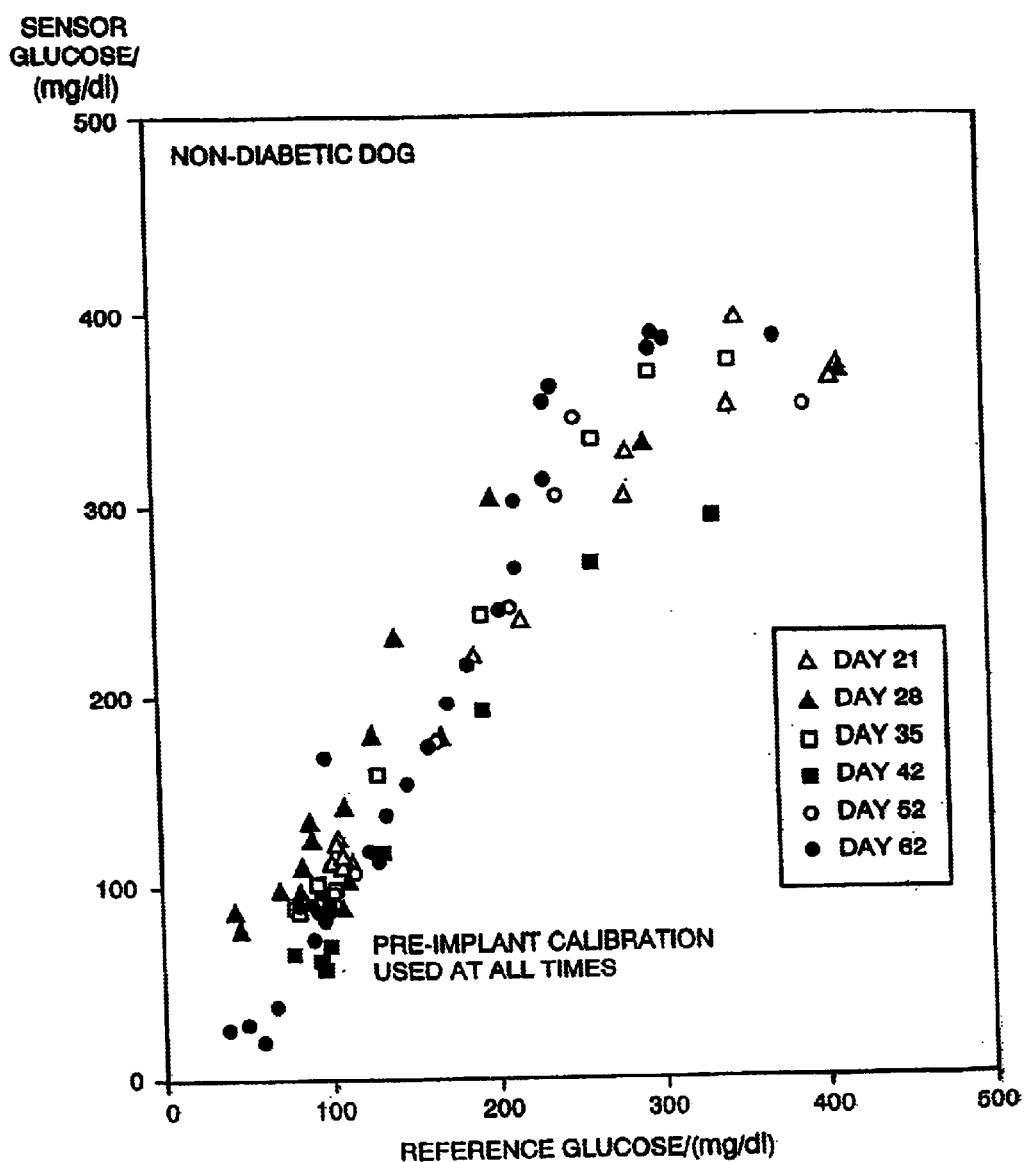
FIG. 3 graphically depicts a correlation plot (days 21 to 62) of a glucose infusion study with one device of the present invention.

This was done in this example via infusion of a 15 g bolus of 50% sterile Dextrose given intravenously in less than about 20 seconds. Reference blood glucose data was then taken from a different vein at 2–5 minute intervals for up to 2 hours after bolus infusion. FIG. 3 depicts correlation plots of six bolus infusion studies, at intervals of 7–10 days on one sensor of the present invention. Sensor glucose concentrations are calculated using a single 37° C. in vitro preimplantation calibration. The sensor response time is accounted for in calculating the sensor glucose concentrations at times of reference blood sampling by time shifting the sensor data 4 minutes.

As with any analytical system, periodic calibration should be performed with the devices of the present invention. Thus, the present invention contemplates some interval of calibration and/or control testing to meet analytical, clinical and regulatory requirements.

EXAMPLE 6

This example describes experiments directed at sensor accuracy and long-term glucose sensor response of several sensor devices contemplated by the present invention.

Pre-implant In vitro Evaluation

Figure 4:
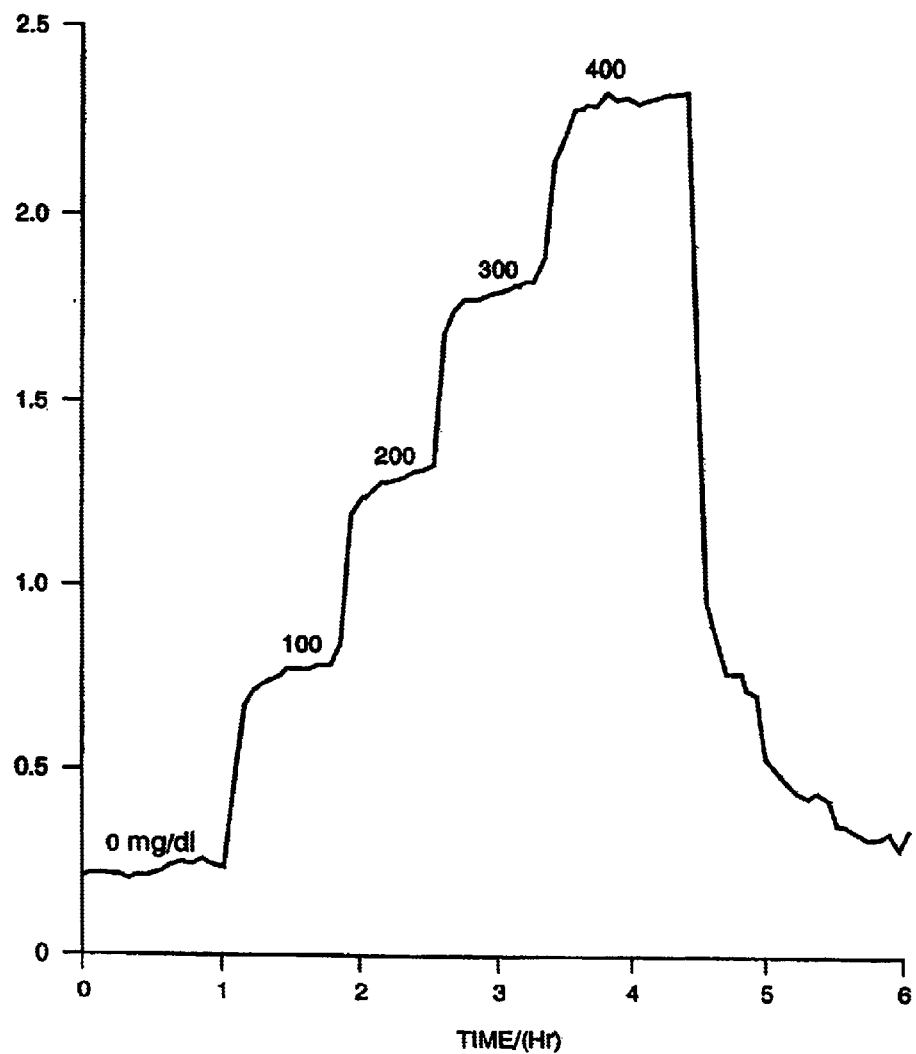
FIG. 4 depicts a typical response to in vitro calibration to glucose of a device of the present invention.

In vitro testing of the sensor devices was accomplished in a manner similar to that previously described. [Gilligan et al., Diabetes Care 17:882–887 (1994)]. Briefly, sensor performance was verified by demonstrating linearity to 100 mg/dL glucose concentration steps from 0 mg/dL through 400 mg/dL (22 mM) with a 90% time response to the glucose steps of less than 5 minutes. A typical satisfactory response to this protocol is shown in FIG. 4. Modulating dissolved oxygen concentration from a $pO_2$ of 150 down to 30 mm Hg (0.25 to 0.05 mM) showed no more than a 10% drop in sensor output at 400 mg/dL for the preferred sensor devices of the present invention. Stability of calibration was maintained within 10% for one week before the final bioprotective and angiogenesis membranes were added to finalize the implant package. A final calibration check was made and had to be within 20% of the prior results for the sensor to be passed on to the implant stage. These final calibration factors (linear least squares regression for the zero glucose current and output to 100 mg/dL current) are used for the initial in vivo calibration. Sensor devices were then wet sterilized with 0.05% thimerosal for 24 hours just prior to implantation.

In vivo Testing

Six sensor devices meeting the parameters described above were surgically implanted under general anesthesia (pentothal induction to effect, followed by halothane maintenance) into the paravertebral subcutaneous tissue of the same mongrel non-diabetic dog. A two-inch skin incision was made several inches from the spine for each implant allowing the creation of a tight-fitting subcutaneous pouch by blunt dissection. The implant was then inserted into the pouch in sensor-down configuration. Subcutaneous tissue was then closed with 3-0 vicryl and skin with 2-0 nylon. Animals were closely monitored for discomfort after surgery and analgesics administered if necessary.

These sensor devices were implanted two-at-a-time in the same dog at approximately six week intervals. Four of the sensor devices were covered with a PTFE-comprising angiogenic layer (these sensor devices were designated Sensors 1901, 1902, 1903, and 1905), while two of the sensor devices served as control sensor devices and did not contain an angiogenic layer, i.e., they contained a bioprotective membrane and the underlying sensor interface structures, as previously described (these sensor devices were designated Sensors 1904 and 1906). To insure anchoring of the device into the subcutaneous tissue, the sensor-side of each implant, except for just over the tip of the sensor, was jacketed in surgical grade double velour polyester fabric (Meadox Medical, Inc.). All sensor devices were tracked after implantation at four-minute intervals using radiotelemetry to follow the long-term sensor response to normoglycemia, allowing verification of the long-term stability of the sensors. To screen for sensor response to changing glucose on selected days following implantation, the response to 0.5 mg glucagon administered subcutaneously was assessed. Responding sensors were identified by a characteristically stable signal prior to glucagon administration followed by a substantial increase in signal within 20 minutes of glucagon injection. The sensor transients then reversed and returned to the prior signal levels within one hour after glucagon injection.

To determine in vivo sensor response times, short-term stability, linearity to glucose concentration, and possible oxygen cofactor limitation effects, glucose infusion studies of up to five hours duration were performed on the dog. These studies were run approximately once every three weeks. The dog was pretrained to rest comfortably and was fully alert during this testing. These experiments used the somatostatin analog octreotide (SANDOSTATIN®, Sandoz) to inhibit the release of insulin, allowing for a slow ramping of blood glucose to the 400–500 mg/dL concentration range.

Sensors were monitored at 32-second intervals to allow simultaneous tracking of up to six sensor devices. In this protocol, octreotide was injected (36–50 $\mu$g/kg) 15–20 minutes before initiation of the glucose infusion. Two peripheral veins were cannulated in the dog to allow for glucose infusion and blood glucose sampling. Ten percent dextrose (0.55 mM) was continuously infused at gradually increasing rates to provide smooth increases in blood glucose from the approximate fasting glucose concentration of about 100 mg/dL to greater than 400 mg/dL. This infusion protocol provides sensor glucose concentration data which can be correlated with reference plasma glucose values when blood samples were drawn from the animal every 5-to-10 minutes. The primary reference glucose determinations were made using a hexokinase method on the DuPont Dimension AR®. A DIRECT 30/30® meter (Markwell Medical) was also used during the course of the experiment to serve as a secondary monitor for the reference blood glucose values and estimate when 400 mg/dL had been reached. At this point the glucose infusion pump was turned off and the blood glucose allowed to return to its normal level.

An additional variation of the protocol described above involved studying the effects of insulin administration on blood glucose concentration prior to the octreotide injection. For these studies 5 units of insulin were injected intravenously, the blood glucose tracked down to 40 mg/dl with the DIRECT 30/30® (Markwell Medical), the octreotide injection made as before, and the infusion pump then started. While the initial glucose pump rate was the same, it was increased faster than before to counteract the insulin and to maintain the same experimental timing.

Once studies were completed, the data was initially analyzed using the final in vitro sensor calibration factors to calculate the implanted sensor glucose concentration. If changes were needed in these factors to optimize the linear regression of sensor to reference blood glucose they were made and noted and followed over the lifetime of the sensor device.

At varying points in time, the implanted sensor devices became less than optimal and were then explanted to determine the underlying cause (less than optimal was defined as the inability to accurately track glucose infusion during two successive tests). Explantation surgical protocols were very similar to those used in the implantation procedure except that the foreign body capsule was opened around the perimeter of the oval implant. The back and sides of the housing had no tissue attachment (as they were not covered with polyester velour), and thus easily separated from the surrounding tissue. The top of the sensor device with attached capsule was then carefully cut free from the subcutaneous tissues.

Once explanted, the sensor devices were carefully examined under a dissecting microscope to look at the state of the capsule tissue contacting the sensor membranes. Once this had been characterized and documented, the tissue was carefully removed from the membrane surface and saved for histological examination. If sensor visualization demonstrated intact membrane layers an initial in vitro calibration check was performed. The sensors were then disassembled from the top membrane down (i.e., from the membrane furthest from the electrodes) with a glucose and hydrogen peroxide calibration check made after removal of each layer. This allowed differentiation of the mechanisms leading to less than optimal results in the membranes and determination of whether processes such as environmental stress cracking, biofouling, or loss of enzyme activity were occurring.

Results And Conclusions
Typical Glucose Infusion Studies

Figure 5A:
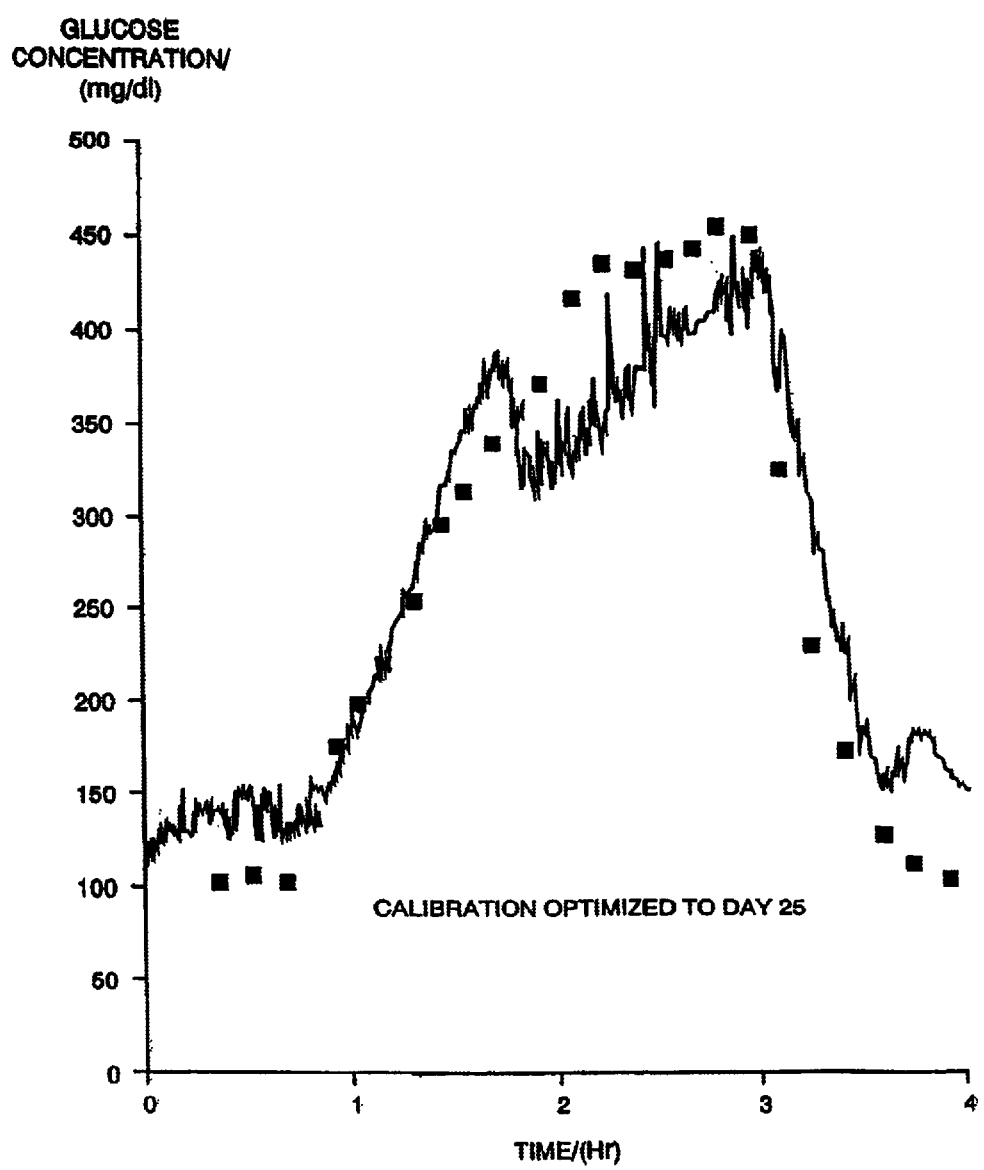
FIGS. 5A, 5B, and 5C graphically depict three in vivo sensor response curves plotted in conjunction with the reference blood glucose values for one device of the present invention at post-implant times of 25, 88, and 109 days.
Figure 5B:
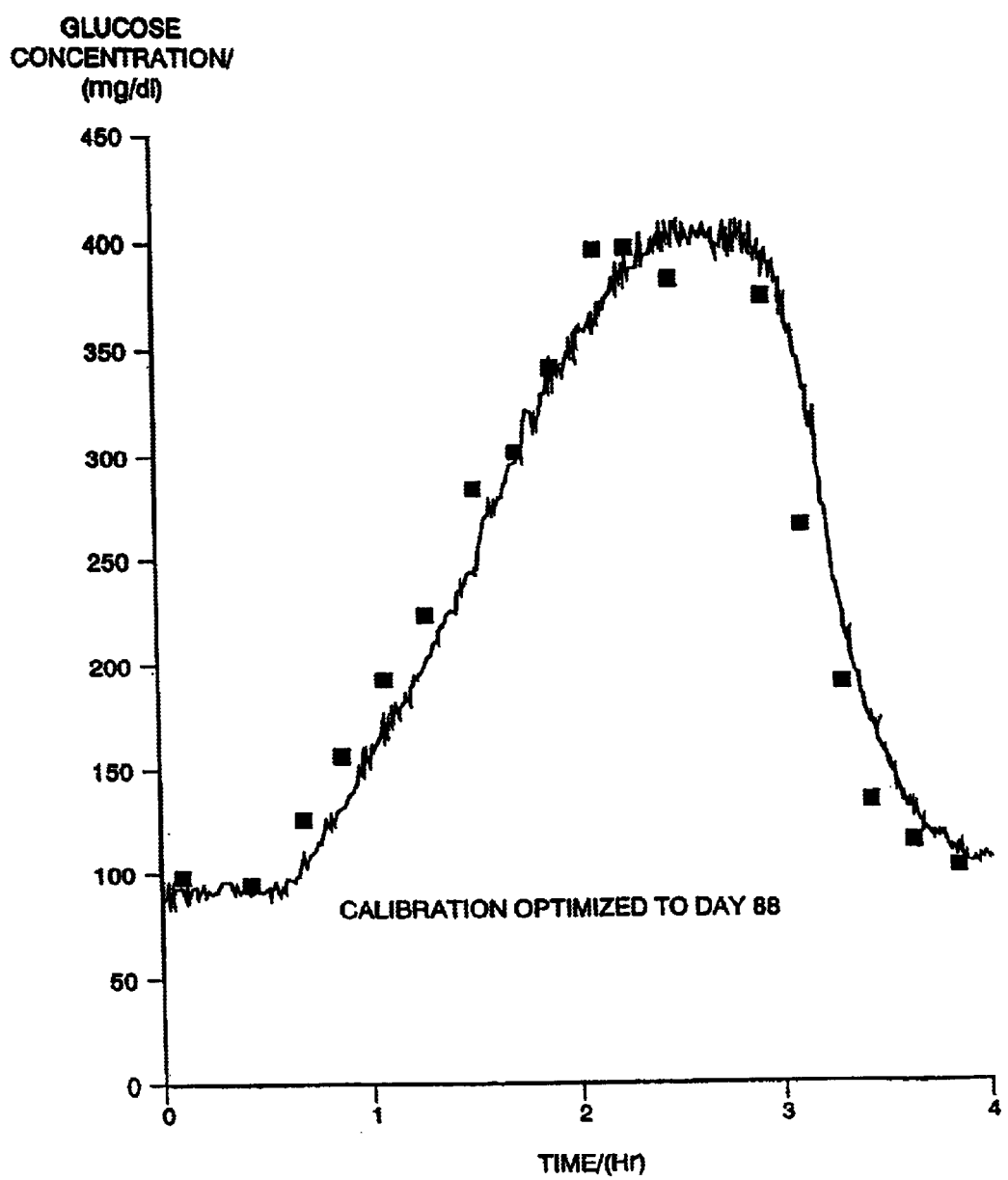
Figure 5C:
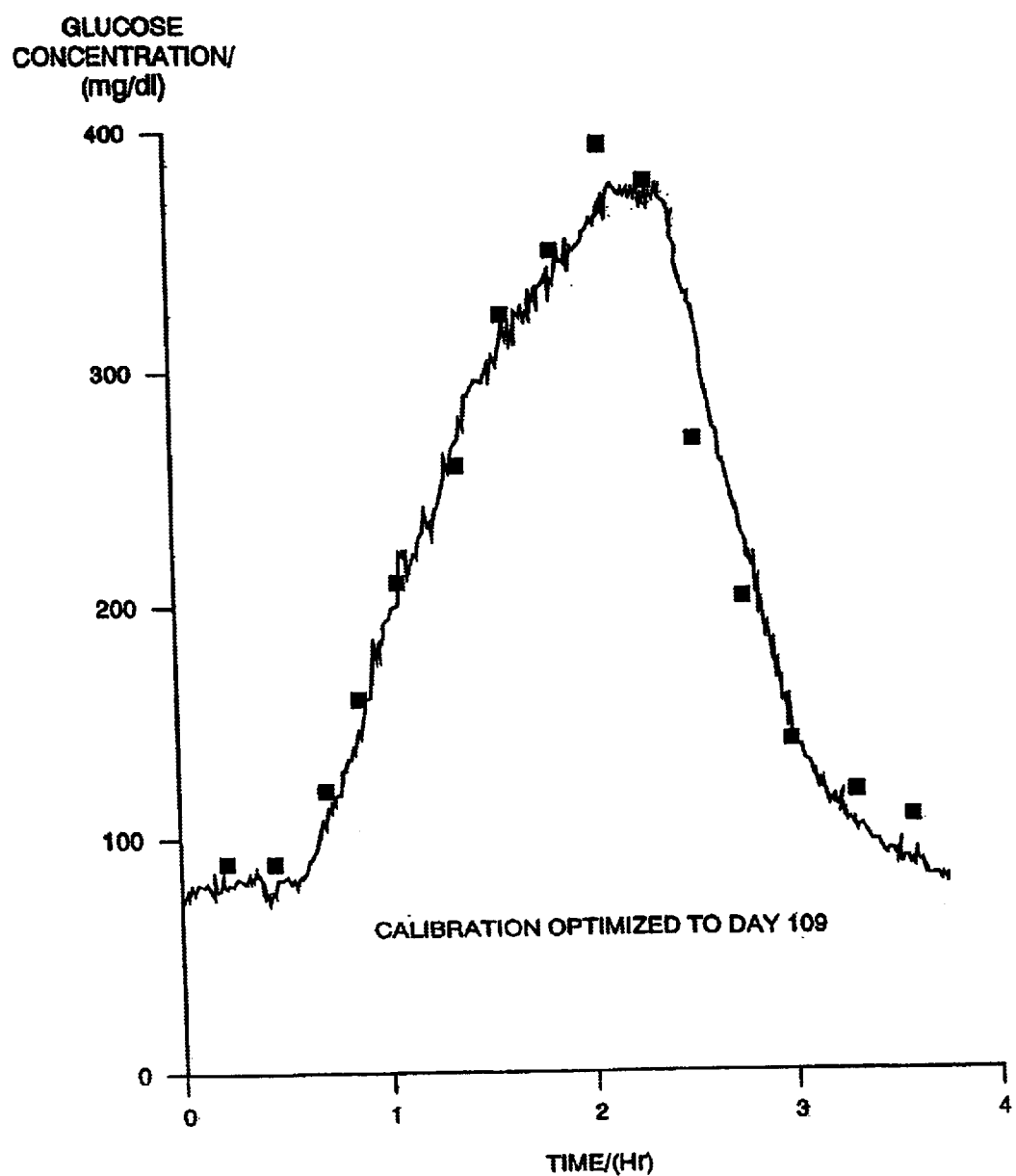

The six sensor devices were tracked for 20–150 days and were evaluated using the octreotide-glucose infusion protocol. FIGS. 5A, 5B, and 5C graphically depict three in vivo sensor response curves (using best case calibration factors) plotted in conjunction with the reference blood glucose values for Sensor 1903 at post-implant times of 25, 88, and 109 days; this data is representative of the data obtainable with the sensor devices of the present invention. Referring to FIGS. 5A–C, the arrow labelled "#1" indicates octreotide injection, the arrow labelled "#2" indicates the turning on of the glucose infusion pump, and the arrow labelled "#3" indicates the turning off of this pump. The 90% response time for this sensor over its lifetime ranged from 5-to-10 minutes and was 5 minutes for the data shown. Such time responses are adequate, since changes in diabetic patients occur at slower rates than used with infusion protocols.

Figure 6:
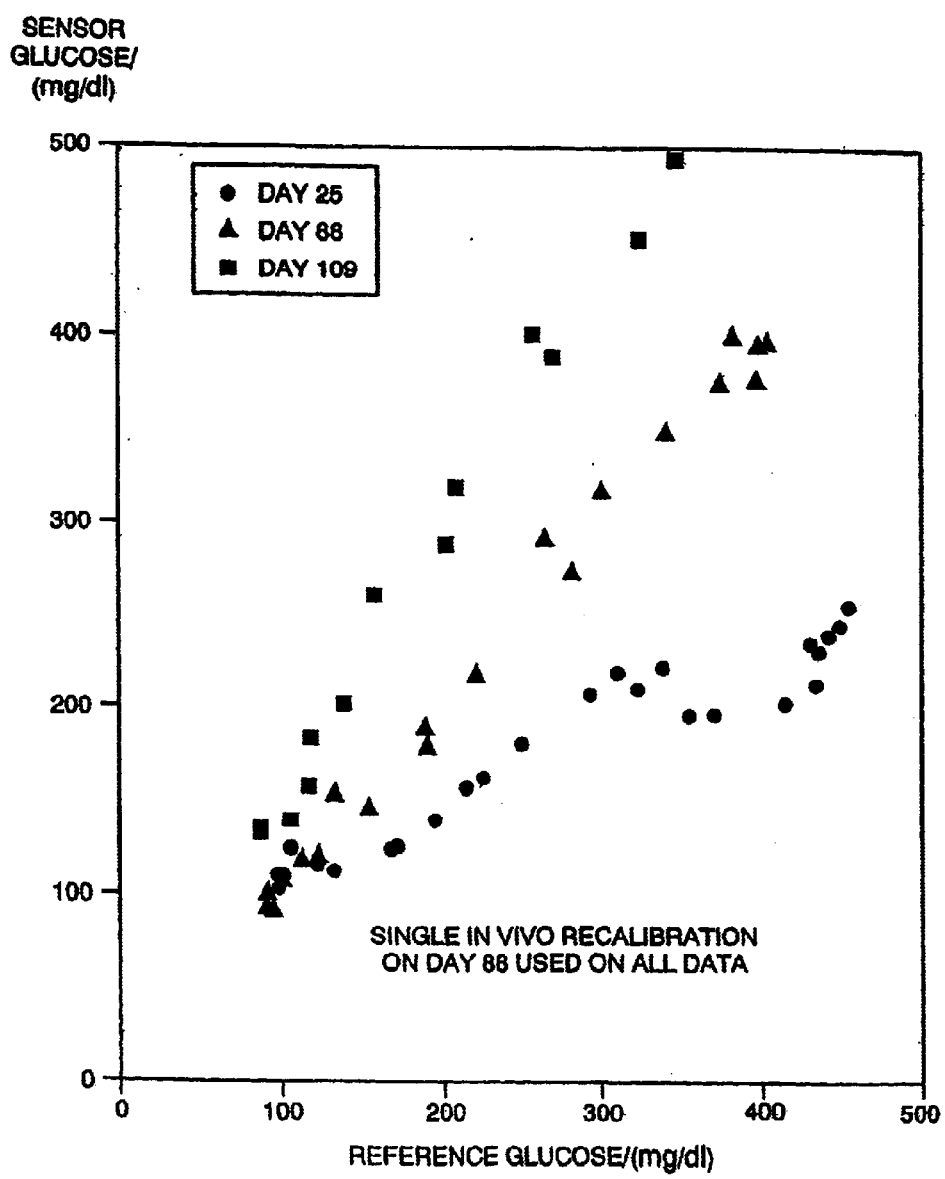
FIG. 6 graphically depicts sensor glucose versus reference glucose for one device of the present invention using the single set of calibration factors from day 88 of FIG. 5B.

FIG. 6 graphically depicts sensor glucose versus reference glucose (for Sensor 1903) using the single set of calibration factors from day 88. As depicted in FIG. 6, when sensor glucose is plotted versus reference glucose, the changes in sensor calibration over the lifetime of the sensor become apparent. These changes are reflected primarily in the output sensitivity to a known glucose concentration step while the zero current remained quite stable. The results suggest that in vivo recalibration every month would be preferred for this sensor to provide optimal glucose tracking.

Performance Comparisons
Angiogenesis Stimulating Membrane Sensors vs. Control Membrane Sensors Generally speaking, demonstration of improvement in a sensor can be judged by noting whether significant improvements in sensor start up time, increased yields of operating glucose sensors, extension of sensor lifetimes, and maintenance of calibration factors occurs. The lifetime of a glucose sensor can be defined as the time of first glucose sensing (in this case during a glucagon challenge) to the last glucose infusion study which provides correct glucose trends to concentration changes. All sensors showed glucose tracking and only one sensor showed a duration of less than 10 days. Average sensor lifetimes of 84±55 days were observed with the sensors containing the angiogenesis-stimulating membrane, values superior to the control sensors which only showed lifetimes of 35±10 days. In addition, one of the sensors incorporating the angiogenic membrane provided optimal data to 150 days.

The description and experimental materials presented above are intended to be illustrative of the present invention while not limiting the scope thereof. It will be apparent to those skilled in the art that variations and modifications can be made without departing from the spirit and scope of the present invention.

We claim:

1. A device for measuring glucose in a biological fluid, comprising:
   a) a housing comprising an electronic circuit and at least two electrodes operatively connected to said electronic circuit; and
   b) a sensor operably connected to said electrodes of said housing, said sensor comprising an apparatus for determining the amount of glucose in a biological sample, said glucose determining apparatus operably associated with said electrodes and comprising a membrane impregnated with an oxidase, a bioprotective membrane substantially impermeable to macrophages, said bioprotective membrane positioned more distal to said housing than said oxidase impregnated membrane, and an angiogenic layer, said angiogenic layer positioned more distal to said housing than said bioprotective membrane, wherein said sensor protrudes from said housing.

2. The biological fluid measuring device of claim 1, wherein the sensor further comprises a sensor interface dome.

3. The biological fluid measuring device of claim 1, wherein said membrane impregnated with oxidase comprises a resistance layer, an enzyme layer, an interference layer and an electrolyte layer.

4. The biological fluid measuring device of claim 3, wherein said resistance layer comprises a polymer membrane with a oxygen-to-glucose permeability ratio of approximately 200:1.

5. The biological fluid measuring device of claim 3, wherein said interference layer comprises a hydrophobic membrane substantially permeable to hydrogen peroxide.

6. The biological fluid measuring device of claim 3, wherein said interference layer comprises a hydrophobic membrane substantially impermeable to chemical compositions having a molecular weight substantially greater than hydrogen peroxide.

7. The biological fluid measuring device of claim 3, wherein said electrolyte layer comprises a semipermeable hydrophilic coating.

8. The biological fluid measuring device of claim 7, wherein said electrolyte layer comprises a curable copolymer of a urethane polymer and a hydrophilic film-forming polymer.

9. The biological fluid measuring device of claim 1, wherein said bioprotective membrane comprises polypropylene, polysulphone, polytetrafluoroethylene, or poly(ethylene terephthalate).

10. The biological fluid measuring device of claim 1, wherein said bioprotective membrane further comprises pores having a diameter of about 0.4 $\mu$m.

11. The biological fluid measuring device of claim 1, wherein said angiogenic layer is selected from the group consisting of hydrophilic polyvinylidene fluoride, mixed cellulose esters, polyvinyl chloride, polypropylene, polysulphone and polymethacrylate.

12. The biological fluid measuring device of claim 1, further comprising c) a securing element for securing said device to biological tissue, said securing element composed of a material selected from the group consisting of polyester, polypropylene cloth, polytetrafluoroethylene felts and expanded polytetrafluoroethylene.

13. The biological fluid measuring device of claim 12, wherein said securing element comprises a polyester velour.

14. The biological fluid measuring device of claim 1, wherein said housing comprising said electronic circuit is filled with material comprising waxes and resins wherein said waxes and resins secure said electronic circuit within said housing.

15. The device of claim 1, wherein said sensor comprises an interface tip for communicating with the tissue of said host, said tip comprising a fixation domain adapted for substantial fixation of said tip in a foreign body capsule.

16. The device of claim 15, wherein said wherein said sensor tip fixation domain further comprises a capsular attachment layer.

17. The device of claim 16, wherein said capsular attachment layer comprises a porous implantable material.

18. The device of claim 16, wherein said capsular attachment layer comprises one of polyester, velour, expanded polytetrafluoroethylene, polytetrafluoroethylene felts, and polypropylene cloth.

19. The device of claim 16, wherein said capsular attachment layer comprises surgical grade polyester velour.

20. The device of claim 1, wherein said bioprotective membrane comprises polytetrafluoroethylene.

21. The device of claim 1, wherein said angiogenic membrane comprises polytetrafluoroethylene.

22. The device of claim 1, wherein said bioprotective membrane and said angiogenic layer are formed from a polytetrafluoroethylene.

23. The device of claim 1, wherein said bioprotective membrane comprises pores having diameter ranging from about 0.1 micron to about 1.0 micron.

24. The device of claim 1, wherein said bioprotective membrane comprises pores having diameter ranging from about 0.2 micron to about 0.5 micron.

25. The device of claim 1, wherein said electronic circuit operably connected to at least one of said electrodes is adapted for continuous, long-term operation.

26. The device of claim 1, wherein said housing further comprises an apparatus operatively connected to said electronic circuit for transmitting data to a location external to said device.

27. The device of claim 26, wherein said data transmitting apparatus comprises radiotelemetry.

28. The device of claim 1, wherein said device is wholly implantable.

29. The device of claim 28, wherein said device is sized and configured for being wholly implantable subcutaneously.

30. The device of claim 1, wherein said housing is substantially oval-shaped.

31. A wholly implantable glucose monitoring device, comprising:
   a) a housing of size and configuration for whole implantation into a host; and
   b) a sensor supported by said housing for communication with tissue of said host, said sensor comprising (i) a member for determining the amount of glucose in biological fluid of said host, and (ii) a bioprotective member disposed more distal to said housing than said glucose determining member and comprising a bioprotective membrane that is substantially impermeable to macrophages and permeable to glucose and oxygen; and
   c) a member for securing the device to biological tissue of said host, said securing member cooperatively associated with said housing, and wherein said securing member comprises poly(ethylene terephthalate).

32. An implantable glucose monitoring device of claim 31, wherein said bioprotective membrane comprises pores, said pores having diameters ranging from about 0.1 micron to about 1.0 micron.

33. An implantable glucose monitoring device of claim 31, wherein said bioprotective membrane comprises polytetrafluoroethylene.

34. An implantable glucose monitoring device of claim 31, wherein said glucose determining member comprises a membrane containing glucose oxidase, said glucose oxidase-containing membrane positioned more proximal to said housing than said bioprotective member.

35. The device of claim 34, wherein said oxidase impregnated membrane comprises a single homogeneous structure.

36. The device of claim 35, wherein said glucose oxidase impregnated membrane comprises a resistance layer, and enzyme layer, an interference layer and an electrolyte layer.

37. The device of claim 36, wherein said resistance layer restricts the transport of glucose therethrough.

38. The device of claim 37, wherein said resistance layer comprises a polymer membrane with a oxygen-to-glucose permeability ratio of approximately 200:1.

39. The device of claim 36, wherein said interference layer comprises a hydrophobic membrane substantially permeable to hydrogen peroxide.

40. The device of claim 39, wherein said interference layer comprises a hydrophobic membrane substantially impermeable to chemical compositions having a molecular weight substantially greater than hydrogen peroxide.

41. The device of claim 37, wherein said electrolyte layer comprises a semipermeable hydrophilic coating.

42. The device of claim 41, wherein said electrolyte layer comprises a curable copolymer of a urethane polymer and a hydrophilic film-forming polymer.

43. An implantable glucose monitoring device of claim 31, wherein said device further comprises at least two electrodes supported by said housing and operably connected to said sensor.

44. An implantable glucose monitoring device of claim 43, wherein said device further comprises electronic circuitry operably connected to at least one of said electrodes and adapted for long-term operation.

45. The device of claim 44, wherein said housing comprising said electronic circuitry is filled with material comprising waxes and resins wherein said waxes and resins secure said electronic circuit within said housing.

46. The device of claim 44, wherein said housing further comprises an apparatus operatively connected to said electronic circuitry for transmitting data to a location external to said device.

47. The device of claim 46, wherein said data transmitting apparatus comprises radiotelemetry.

48. An implantable glucose monitoring device of claim 48, said housing comprising a cavity contained therewithin.

49. An implantable glucose monitoring device of claim 48, wherein said sensor is within said housing cavity.

50. The device of claim 31, wherein said sensor comprises an interface tip for communicating with the tissue of said host, said tip comprising a fixation domain adapted for substantial fixation of said tip in a foreign body capsule.

51. The device of claim 50, wherein said wherein said fixation domain further comprises a capsular attachment layer.

52. The device of claim 51, wherein said capsular attachment layer comprises a porous implantable material.

53. The device of claim 51, wherein said capsular attachment layer comprises one of polyester, velour, expanded polytetrafluoroethylene, polytetrafluoroethylene felts, and polypropylene cloth.

54. The device of claim 51, wherein said capsular attachment layer comprises surgical grade polyester velour.

55. The device of claim 31, further comprising an angiogenic layer positioned more distal to said housing than said bioprotective membrane.

56. The device of claim 55, wherein said angiogenic layer comprises one of hydrophilic polyvinylidene fluoride, mixed cellulose esters, polyvinyl chloride, polypropylene, polysulphone and polymethacrylate.

57. The device of claim 55, wherein said angiogenic layer comprises polytetrafluoroethylene.

58. The device of claim 55, wherein said bioprotective and angiogenic layers are formed from a polytetrafluoroethylene.

59. The device of claim 31, wherein said bioprotective membrane comprises one of polypropylene, polysulphone, polytetrafluoro ethylene, and poly(ethylene terephthalate).

60. The device of claim 31, wherein said device is sized and configured for being wholly implantable subcutaneously.

61. The device of claim 31, wherein said housing is substantially oval-shaped.

62. The device of claim 31, wherein said sensor further comprises a sensor interface dome that protrudes from said housing.

63. A biological fluid measuring device, comprising:
   (a) a housing comprising an electronic circuit and at least two electrodes operably connected to said electronic circuit; and
   (b) a sensor operably connected to said electrodes of said housing, said sensor comprising (i) a bioprotective membrane, and (ii) an angiogenic layer said angiogenic layer positioned more distal to said housing than said bioprotective membrane, wherein said angiogenic layer comprises polytetrafluoroethylene.

64. The biological fluid measuring device of claim 63, wherein said bioprotective membrane is substantially impermeable to macrophages.

65. The biological fluid measuring devise of claim 63, wherein said bioprotective membrane comprises pores, said pores having diameters ranging from about 0.1 micron to about 1.0 micron.

66. The biological fluid measuring device of claim 63, wherein said bioprotective membrane comprises polytetrafluoroethylene.

67. The biological fluid measuring device of claim 63, further comprising (c) a member for securing said device to biological tissue, and securing member associated with said housing.

68. The biological fluid measuring device of claim 67, wherein said securing member comprises poly(ethylene terephthalate).

69. The biological fluid measuring device of claim 63, wherein said sensor further comprises a member for determining the amount of glucose in a biological sample.

70. The biological fluid measuring device of claim 69, wherein said glucose determining member comprises a membrane containing glucose oxidase, said glucose oxidase-containing membrane positioned more proximal to said housing than said bioprotective membrane.

71. The device of claim 70, wherein said glucose oxidase-containing membrane comprises a resistance layer, and enzyme layer, an interference layer and an electrolyte layer.

72. The device of claim 71, wherein said resistance layer restricts the transport of glucose therethrough.

73. The device of claim 71, wherein said resistance layer comprises a polymer membrane with a oxygen-to-glucose permeability ratio of approximately 200:1.

74. The device of claim 71, wherein said interference layer comprises a hydrophobic membrane substantially permeable to hydrogen peroxide.

75. The device of claim 74, wherein said interference layer comprises a hydrophobic membrane substantially impermeable to chemical compositions having a molecular weight substantially greater than hydrogen peroxide.

76. The device of claim 74, wherein said electrolyte layer comprises a semipermeable hydrophilic coating.

77. The device of claim 76, wherein said electrolyte layer comprises a curable copolymer of a urethane polymer and a hydrophilic film-forming polymer.

78. The device of claim 70, wherein said glucose oxidase-containing membrane comprises a single homogeneous structure.

79. The device of claim 67, wherein said securing member comprises one of polyester, polypropylene cloth, polytetrafluoroethylene felts and expanded polytetrafluoroethylene.

80. The device of claim 67, wherein said securing member comprises a polyester velour.

81. The device of claim 63, wherein said housing comprising said electronic circuit is filled with material comprising waxes and resins wherein said waxes and resins secure said electronic circuit within said housing.

82. The device of claim 81, wherein said data transmitting apparatus comprises radiotelemetry.

83. The device of claim 63, wherein said sensor further comprises an interface tip for communicating with the tissue of said host, said tip comprising a fixation domain adapted for substantial fixation of said tip in a foreign body capsule.

84. The device of claim 83, wherein said wherein said sensor tip fixation domain further comprises a capsular attachment layer.

85. The device of claim 84, wherein said capsular attachment layer comprises a porous implantable material.

86. The device of claim 84, wherein said capsular attachment layer comprises one of polyester, velour, expanded polytetrafluoroethylene, polytetrafluoroethylene felts, and polypropylene cloth.

87. The device of claim 84, wherein said capsular attachment layer comprises surgical grade polyester velour.

88. The device of claim 63, wherein said bioprotective membrane comprises one of polypropylene, polysulphone, polytetrafluoroethylene, and poly(ethylene terephthalate).

89. The device of claim 63, wherein said electronic circuit operably connected to said at least two electrodes is adapted for long-term operation.

90. The device of claim 63, wherein said device is wholly implantable.

91. The device of claim 90, wherein said device is sized and configured for being wholly implantable subcutaneously.

92. The device of claim 63, wherein said housing is substantially oval-shaped.

93. The device of claim 63, wherein said sensor further comprises a sensor interface dome that protrudes from said housing.

94. A device for measuring glucose in a tissue of a host comprising:
a wholly implantable device comprising a sensor having an interface tip for communicating with the tissue of said host, said tip comprising a fixation domain adapted for substantial fixation of said tip in a foreign bode capsule, wherein said sensor tip fixation domain comprises a capsular attachment layer on said sensor, and wherein said sensor tip fixation domain further comprises an angiogenic layer on said sensor.

95. The device of claim 94, wherein said wholly implantable device is sized and configured for being wholly implanted subcutaneously.

96. The device of claim 94, wherein said capsular attachment layer comprises surgical grade polyester velour.

97. The device of claim 94, further comprising a securing element for securing said device to biological tissue.

98. The device of claim 97, wherein said securing element comprises one of polyester, polypropylene cloth, polytetrafluoroethylene felts and expanded polytetrafluoroethylene.

99. The device of claim 98, wherein said securing element comprises a polyester velour.

100. The device of claim 94, wherein said capsular attachment layer comprises a porous implantable material.

101. The device of claim 94, wherein said capsular attachment layer comprises one of polyester, velour, expanded polytetrafluoroethylene, polytetrafluoroethylene felts, and polypropylene cloth.

102. The device of claim 94, wherein said angiogenic layer comprises one of hydrophilic polyvinylidene fluoride, mixed cellulose esters, polyvinyl chloride, polypropylene, polysulphone and polymethacrylate.

103. The device of claim 94, wherein said angiogenic layer comprises polytetrafluoroethylene.

104. The device of claim 94, further comprising a bioprotective membrane substantially impermeable to macrophages, said bioprotective membrane located proximal to said angiogenic layer.

105. The device of claim 106, wherein said bioprotective membrane comprises polytetrafluoroethylene.

106. The device of claim 104, wherein said bioprotective and angiogenic layers are formed from a polytetrafluoroethylene.

107. The device of claim 104, wherein said bioprotective membrane comprises pores having diameter ranging from about 0.1 micron to about 1.0 micron.

108. The device of claim 104, wherein said bioprotective membrane comprises pores having diameter ranging from about 0.2 micron to about 0.5 micron.

109. The device of claim 104, wherein said bioprotective membrane comprises one of polypropylene, polysulphone, polytetrafluoroethylene, and poly(ethylene terephthalate).

110. The device of claim 94, further comprising a membrane impregnated with an oxidase located proximal to said angiogenic layer.

111. The device of claim 110, wherein said oxidase impregnated membrane comprises a resistance layer, and enzyme layer an interference layer and an electrolyte layer.

112. The device of claim 111, wherein said resistance layer restricts the transport of glucose therethrough.

113. The device of claim 112, wherein said resistance layer comprises a polymer membrane with a oxygen-to-glucose permeability ratio of approximately 200:1.

114. The device of claim 111, wherein said interference layer comprises a hydrophobic membrane substantially permeable to hydrogen peroxide.

115. The device of claim 114, wherein said interference layer comprises a hydrophobic membrane substantially impermeable to chemical compositions having a molecular weight substantially greater than hydrogen peroxide.

116. The device of claim 111, wherein said electrolyte layer comprises a semipermeable hydrophilic coating.

117. The device of claim 116, wherein said electrolyte layer comprises a curable copolymer of a urethane polymer and a hydrophilic film-forming polymer.

118. The device of claim 111, wherein said enzyme layer contains glucose oxidase.

119. The device of claim 110, wherein said oxidase impregnated membrane comprises a single homogeneous structure.

120. The device of claim 94, further comprising a housing that has an electronic circuit and at least two electrodes operatively connected to said electronic circuit, wherein said sensor is operably connected to said electrodes of said housing.

121. The device of claim 120, wherein said housing comprising said electronic circuit is filled with material comprising waxes and resins wherein said waxes and secure said electronic circuit within said housing.

122. The device of claim 120, wherein said electronic circuit operably connected to at least one of said electrodes is adapted for long-term operation.

123. The device of claim 120, wherein said housing further comprises an apparatus operatively connected to said electronic circuit for transmitting data to a location external to said device.

124. The device of claim 123, wherein said data transmitting apparatus comprises radiotelemetry.

125. The device of claim 94, wherein said device is sized and configured for being wholly implantable subcutaneously.

126. The device of claim 94, wherein said housing is substantially oval-shaped.

127. The device of claim 94, wherein said sensor interface tip comprises a dome configuration.

128. The device of claim 127, wherein said sensor interface tip protrudes from said housing.

129. An implantable device for subcutaneous monitoring of glucose levels, comprising a housing and a sensor comprising an angiogenic layer for promoting adequate microcirculatory delivery of glucose and oxygen to said sensor, wherein said sensor further comprises a capsular attachment layer.

130. The device of claim 129, wherein said implantable device is sized and configured for being wholly implanted subcutaneously.

131. The device of claim 129, further comprising a securing element for securing said device to biological tissue.

132. The device of claim 131, wherein said securing element comprises one of polyester, polypropylene cloth, polytetrafluoroethylene felts and expanded polytetrafluoroethylene.

133. The device of claim 132, wherein said securing element comprises a polyester velour.

134. The device of claim 129, wherein said angiogenic layer comprises one of hydrophilic polyvinylidene fluoride, mixed cellulose esters, polyvinyl chloride, polypropylene, polysulphone and polymethacrylate.

135. The device of claim 129, wherein said angiogenic layer comprises polytetrafluoroethylene.

136. The device of claim 129 further comprising a bioprotective membrane substantially impermeable to macrophages, said bioprotective membrane located proximal to said angiogenic layer.

137. The device of claim 136, wherein said bioprotective membrane comprises polytetrafluoroethylene.

138. The device of claim 136, wherein said bioprotective and angiogenic layers are formed from a polytetrafluoroethylene.

139. The device of claim 136, wherein said bioprotective membrane comprises pores having diameter ranging from about 0.1 micron to about 1.0 micron.

140. The device of claim 136, wherein said bioprotective membrane comprises pores having diameter ranging from about 0.2 micron to about 0.5 micron.

141. The device of claim 136, wherein said bioprotective membrane comprises one of polypropylene, polysulphone, polytetrafluoroethylene, and poly(ethylene terephthalate).

142. The device of claim 129, said sensor further comprising a membrane impregnated with an oxidase.

143. The device of claim 142, wherein said oxidase impregnated membrane comprises a resistance layer, and enzyme layer, an interference layer and an electrolyte layer.

144. The device of claim 142, wherein said oxidase impregnated membrane comprises a single homogeneous structure.

145. The device of claim 143, wherein said resistance layer restricts the transport of glucose therethrough.

146. The device of claim 145, wherein said resistance layer comprises a polymer membrane with a oxygen-to-glucose permeability ratio of approximately 200:1.

147. The device of claim 143, wherein said interference layer comprises a hydrophobic membrane substantially permeable to hydrogen peroxide.

148. The device of claim 143, wherein said interference layer comprises a hydrophobic membrane substantially impermeable to chemical compositions having a molecular weight substantially greater than hydrogen peroxide.

149. The device of claim 143, wherein said electrolyte layer comprises a semipermeable hydrophilic coating.

150. The device of claim 143, wherein said electrolyte layer comprises a curable copolymer of a urethane polymer and a hydrophilic film-forming polymer.

151. The device of claim 143, wherein said enzyme layer contains glucose oxidase.

152. The device of claim 129, wherein said housing comprises an electronic circuit and at least two electrodes operatively connected to said electronic circuit, and wherein said sensor is operably connected to said electrodes of said housing.

153. The device of claim 152, wherein said housing comprising said electric circuit is filled with material comprising waxes and resins wherein said waxes and resins secure said electronic circuit within said housing.

154. The device of claim 152, wherein said electronic circuit operably connected to at least one of said electrodes is adapted for long-term operation.

155. The device of claim 129, wherein said housing comprises an apparatus operatively connected to said electronic circuit for transmitting data to a location external to said device.

156. The device of claim 155, wherein said data transmitting apparatus comprises radiotelemetry.

157. The device of claim 129, wherein said device is sized and configured for being wholly implantable subcutaneously.

158. The device of claim 129, wherein said housing is substantially oval-shaped.

159. The device of claim 129, wherein said sensor comprises an interface tip that has a dome configuration.

160. The device of claim 159, wherein said interface tip protrudes from said housing.

161. A device for measuring glucose in a biological fluid, comprising:
a) a housing comprising an electronic circuit and at least two electrodes operatively connected to said electronic circuit; and
b) a sensor operably connected to said electrodes of said housing, said sensor comprising an apparatus for determining the amount of glucose in a biological sample, said glucose determining apparatus operably associated with said electrodes and comprising a membrane impregnated with an oxidase, a bioprotective membrane substantially impermeable to macrophages, said bioprotective membrane positioned more distal to said housing than said oxidase impregnated membrane, and an angiogenic layer positioned more distal to said housing than said bioprotective membrane, wherein the sensor further comprises a sensor interface dome.

162. The device of claim 161, further comprising c) a securing element for securing said device to biological tissue.

163. The device of claim 162, wherein said securing element comprises one of polyester, polypropylene cloth, polytetrafluoroethylene felts and expanded polytetrafluoroethylene.

164. The device of claim 162, wherein said securing element comprises a polyester velour.

165. The device of claim 161, wherein said sensor interface dome comprises an interface tip for communicating with the tissue of said host, said tip comprising a fixation domain adapted for substantial fixation of said tip in a foreign body capsule.

166. The device of claim 165, wherein said wherein said fixation domain further comprises a capsular attachment layer.

167. The device of claim 166, wherein said capsular attachment layer comprises a porous implantable material.

168. The device of claim 166, wherein said capsular attachment layer comprises one of polyester, velour, expanded polytetrafluoroethylene, polytetrafluoroethylene felts, and polypropylene cloth.

169. The device of claim 166, wherein said capsular attachment layer comprises surgical grade polyester velour.

170. The device of claim 161, wherein said angiogenic layer comprises one of hydrophilic polyvinylidene fluoride, and mixed cellulose esters.

171. The device of claim 161, wherein said angiogenic layer comprises one of polyvinyl chloride, polypropylene, polysulphone, and polymethacrylate.

172. The device of claim 161, wherein said bioprotective membrane comprises polytetrafluoroethylene.

173. The device of claim 161, wherein said angiogenic layer comprises polytetrafluoroethylene.

174. The device of claim 161, wherein said bioprotective and angiogenic layers are formed from a polytetrafluoroethylene.

175. The device of claim 161, wherein said bioprotective membrane comprises pores having diameter ranging from about 0.1 micron to about 1.0 micron.

176. The device of claim 161, wherein said bioprotective membrane comprises pores having diameter ranging forming about 0.2 micron to about 0.5 micron.

177. The device of claim 161, wherein said bioprotective membrane comprises one of polypropylene, polysulphone, polytetrafluoroethylene, and poly(ethylene terephthalate).

178. The device of claim 161, wherein said oxidase impregnated membrane comprises a single homogeneous structure.

179. The device of claim 161, wherein said oxidase impregnated membrane comprises a resistance layer, and enzyme layer, an interference layer and an electrolyte layer.

180. The device of claim 179, wherein said resistance layer restricts the transport of glucose therethrough.

181. The device of claim 179, wherein said resistance layer comprises a polymer membrane with a oxygen-to-glucose permeability ratio of approximately 200:1.

182. The device of claim 179, wherein said interference layer comprises a hydrophobic membrane substantially permeable to hydrogen peroxide.

183. The device of claim 179, wherein said interference layer comprises a hydrophobic membrane substantially impermeable to chemical compositions having a molecular weight substantially greater than hydrogen peroxide.

184. The device of claim 179, said electrolyte layer comprises a semipermeable hydrophilic coating.

185. The device of claim 184, wherein said electrolyte layer comprises a curable copolymer of a urethane polymer and a hydrophilic film-forming polymer.

186. The device of claim 179, wherein said enzyme layer contains glucose oxidase.

187. The device of claim 161, wherein said housing comprising said electronic circuit is filled with material comprising waxes and resins wherein said waxes and resins secure said electronic circuit within said housing.

188. The device of claim 161, wherein said electronic circuit operably connected to at least one of said electrodes is adapted for long-term operation.

189. The device of claim 161, wherein said housing further comprises an apparatus operatively connected to said electronic circuit for transmitting data to a location external to said device.

190. The device of claim 189, wherein said data transmitting apparatus comprises radiotelemetry.

191. The device of claim 161, wherein said device is wholly implantable.

192. The device of claim 191, wherein said device is sized and configured for being wholly implantable subcutaneously.

193. The device of claim 161, wherein said housing is substantially oval-shaped.

194. The device of claim 161, wherein said sensor interface dome protrudes from said housing.

195. A device for measuring glucose in a biological fluid, comprising:
  a) a housing comprising an electronic circuit and at least two electrodes operatively connected to said electronic circuit; and
  b) a sensor operably connected to said electrodes of said housing, said sensor comprising an apparatus for determining the amount of glucose in a biological sample, said glucose determining apparatus operably associated with said electrodes and comprising a membrane impregnated with an oxidase, a bioprotective membrane substantially impermeable to macrophages, said bioprotective membrane positioned more distal to said housing than said oxidase impregnated membrane, and an angiogenic layer positioned more distal to said housing than said bioprotective membrane, wherein said membrane impregnated with oxidase comprises a resistance layer, and enzyme layer, an interference layer and an electrolyte layer.

196. The device of claim 195, further comprising c) a securing element for securing said device to biological tissue.

197. The device of claim 196, wherein said securing element comprises one of polyester, polypropylene cloth, polytetrafluoroethylene felts and expanded polytetrafluoroethylene.

198. The device of claim 196, wherein said securing element comprises a polyester velour.

199. The device of claim 196, wherein said sensor comprises an interface tip for communicating with the tissue of said host, said tip comprising a fixation domain adapted for substantial fixation of said tip in a foreign body capsule.

200. The device of claim 199, wherein said wherein said fixation domain further comprises a capsular attachment layer.

201. The device of claim 200, wherein said capsular attachment layer comprises a porous implantable material.

202. The device of claim 200, wherein said capsular attachment layer comprises one of polyester, velour, expanded polytetrafluoroethylene, polytetrafluoroethylene felts, and polypropylene cloth.

203. The device of claim 200, wherein said capsular attachment layer comprises surgical grade polyester velour.

204. The device of claim 195, wherein said angiogenic layer comprises one of hydrophilic polyvinylidene fluoride, mixed cellulose esters, polyvinyl chloride, polypropylene, polysulphone and polymethacrylate.

205. The device of claim 195, wherein said bioprotective membrane comprises polytetrafluoroethylene.

206. The device of claim 195, wherein said angiogenic layer comprises polytetrafluoroethylene.

207. The device of claim 195, wherein said bioprotective and angiogenic layers are formed from a polytetrafluoroethylene.

208. The device of claim 195, wherein said bioprotective membrane comprises pores having diameter ranging from about 0.1 micron to about 1.0 micron.

209. The device of claim 208, wherein said bioprotective membrane comprises pores having diameter ranging from about 0.2 micron to about 0.5 micron.

210. The device of claim 195, wherein said bioprotective membrane comprises one of polypropylene, polysulphone, polytetrafluoroethylene, and poly(ethylene terephthalate).

211. The device of claim 195, wherein said resistance layer restricts the transport of glucose therethrough.

212. The device of claim 211, wherein said resistance layer comprises a polymer membrane with a oxygen-to-glucose permeability ratio of approximately 200:1.

213. The device of claim 195, wherein said interference layer comprises a hydrophobic membrane substantially permeable to hydrogen peroxide.

214. The device of claim 213, wherein said interference layer comprises a hydrophobic membrane substantially impermeable to chemical compositions having a molecular weight substantially greater than hydrogen peroxide.

215. The device of claim 195, wherein said electrolyte layer comprises a semipermeable hydrophilic coating.

216. The device of claim 215, wherein said electrolyte layer comprises a curable copolymer of a urethane polymer and a hydrophilic film-forming polymer.

217. The device of claim 195, wherein said enzyme layer contains glucose oxidase.

218. The device of claim 195, wherein said housing comprising said electronic circuit is filled with material comprising waxes and resins wherein said waxes and resins secure said electric circuit within said housing.

219. The device of claim 195, wherein said electronic circuit operably connected to at least one of said electrodes is adapted for long-term operation.

220. The device of claim 195, wherein said housing further comprises an apparatus operatively connected to said electronic circuit for transmitting data to a location external to said device.

221. The device of claim 220, wherein said data transmitting apparatus comprises radiotelemetry.

222. The device of claim 195, wherein said device is wholly implantable.

223. The device of claim 222, said device is sized and configured for being wholly implantable subcutaneously.

224. The device of claim 195, wherein said housing is substantially oval-shaped.

225. The device of claim 195, wherein said sensor further comprises a sensor interface dome that protrudes from said housing.

226. A device for measuring glucose in a biological fluid, comprising:
  a) a housing comprising an electronic circuit and at least two electrodes operatively connected to said electronic circuit;
  b) a sensor operably connected to said electrodes of said housing, said sensor comprising an apparatus for determining the amount of glucose in a biological sample, said glucose determining apparatus operably associated with said electrodes and comprising a membrane impregnated with an oxidase, a bioprotective membrane substantially impermeable to macrophages, said bioprotective membrane positioned more distal to said housing than said oxidase impregnated membrane, and an angiogenic layer positioned more distal to said housing than said bioprotective membrane,
  c) a securing element for securing said device to biological tissue, said securing element composed of a material selected from the group consisting of polyester, polypropylene cloth, polytetrafluoroethylene felts and expanded polytetrafluoroethylene.

227. The device of claim 226, wherein said securing element comprises a polyester velour.

228. The device of claim 226, wherein said sensor comprises an interface tip for communicating with the tissue of said host, said tip comprising a fixation domain adapted for substantial fixation of said tip in a foreign body capsule.

229. The device of claim 228, wherein said wherein said fixation domain further comprises a capsular attachment layer.

230. The device of claim 229, wherein said capsular attachment layer comprises a porous implantable material.

231. The device of claim 229, wherein said capsular attachment layer comprises one of polyester, velour, expanded polytetrafluoroethylene, polytetrafluoroethylene felts, and polypropylene cloth.

232. The device of claim 229, wherein said capsular attachment layer comprises surgical grade polyester velour.

233. The device of claim 226, wherein said angiogenic layer comprises one of hydrophilic polyvinylidene fluoride, mixed cellulose esters, polyvinyl chloride, polypropylene, polysulphone and polymethacrylate.

234. The device of claim 226, wherein said bioprotective membrane comprises polytetrafluoroethylene.

235. The device of claim 226, wherein said angiogenic layer comprises polytetrafluoroethylene.

236. The device of claim 226, wherein said bioprotective and angiogenic layers are formed from a polytetrafluoroethylene.

237. The device of claim 226, wherein said bioprotective membrane comprises pores having diameter ranging from about 0.1 micron to about 1.0 micron.

238. The device of claim 226, wherein said bioprotective membrane comprises pores having diameter ranging from about 0.2 micron to about 0.5 micron.

239. The device of claim 226, wherein said bioprotective membrane comprises one of polypropylene, polysulphone, polytetrafluoroethylene, and poly(ethylene terephthalate).

240. The device of claim 226, wherein said oxidase impregnated membrane comprises a resistance layer, and enzyme layer, an interference layer and an electrolyte layer.

241. The device of claim 226, wherein said oxidase impregnated membrane comprises a single homogeneous structure.

242. The device of claim 240, wherein said resistance layer restricts the transport of glucose therethrough.

243. The device of claim 240, wherein said resistance layer comprises a polymer membrane with a oxygen-to-glucose permeability ratio of approximately 200:1.

244. The device of claim 240, wherein said interference layer comprises a hydrophobic membrane substantially permeable to hydrogen peroxide.

245. The device of claim 240, wherein said interference layer comprises a hydrophobic membrane substantially impermeable to chemical compositions having a molecular weight substantially greater than hydrogen peroxide.

246. The device of claim 240, wherein said electrolyte layer comprises a semipermeable hydrophilic coating.

247. The device of claim 246, wherein said electrolyte layer comprises a curable copolymer of a urethane polymer and a hydrophilic film-forming polymer.

248. The device of claim 240, wherein said enzyme layer contains glucose oxidase.

249. The device of claim 226, wherein said housing comprising said electronic circuit is filled with material comprising waxes and resins wherein said waxes and resins secure said electronic circuit within said housing.

250. The device of claim 226, wherein said electronic circuit operably connected to at least one of said electrodes is adapted for long-term operation.

251. The device of claim 226, wherein said housing further comprises an apparatus operatively connected to said electronic circuit for transmitting data to a location external to said device.

252. The device of claim 251, wherein said data transmitting apparatus comprised radiotelemetry.

253. The device of claim 226, wherein said device is wholly implantable.

254. The device of claim 180, wherein said device is sized and configured for being wholly implantable subcutaneously.

255. The device of claim 229, wherein said housing is substantially oval-shaped.

256. The device of claim 226, wherein said sensor further comprises a sensor interface dome that protrudes from said housing.

257. A biological fluid measuring device, comprising:
  a) a housing comprising an electronic circuit and at least two electrodes operably connected to said electronic circuit; and
  b) a sensor operably connected to said electrodes of said housing, said sensor comprising (i) a bioprotective membrane, and (ii) an angiogenic layer, said angiogenic layer positioned more distal to said housing than said bioprotective membrane; and
  c) a member for securing said device to biological tissue, and securing member associated with said housing.

258. The device of claim 257, wherein said securing element comprises one of a material selected from the group consisting of polyester, polypropylene cloth, polytetrafluoroethylene felts and expanded polytetrafluoroethylene.

259. The device of claim 258, wherein said securing element comprises a polyester velour.

260. The device of claim 257, wherein said sensor comprises an interface tip for communicating with the tissue of said host, said tip comprising a fixation domain adapted for substantial fixation of said tip in a foreign body capsule.

261. The device of claim 260, wherein said wherein said fixation domain further comprises a capsular attachment layer.

262. The device of claim 261, wherein said capsular attachment layer comprises a porous implantable material.

263. The device of claim 261, wherein said capsular attachment layer comprises one of polyester, velour, expanded polytetramethylene, polytetrafluoroethylene felts, and polypropylene cloth.

264. The device of claim 261, wherein said capsular attachment layer comprises surgical grade polyester velour.

265. The device of claim 257, wherein said angiogenic layer comprises one of hydrophilic polyvinylidene fluoride, mixed cellulose esters, polyvinyl chloride, polypropylene, polysulphone and polymethacrylate.

266. The device of claim 257, wherein said bioprotective membrane comprises polytetrafluoroethylene.

267. The device of claim 257, wherein said angiogenic layer comprises polytetrafluoroethylene.

268. The device of claim 257, wherein said bioprotective and angiogenic layers are formed from a polytetrafluoroethylene.

269. The device of claim 257, wherein said bioprotective membrane comprises pores having diameter ranging from about 0.1 micron to about 1.0 micron.

270. The device of claim 257, wherein said bioprotective membrane comprises pores having diameter ranging from about 0.2 micron to about 0.5 micron.

271. The device of claim 257, wherein said bioprotective membrane comprises one of polypropylene, polysulphone, polytetrafluoroethylene, and poly(ethylene terephthalate).

272. The device of claim 257, wherein said oxidase impregnated membrane comprises a resistance layer, and enzyme layer, an interference layer and an electrolyte layer.

273. The device of claim 272, wherein said oxidase impregnated membrane comprises a single homogeneous structure.

274. The device of claim 272, wherein said resistance layer restricts the transport of glucose therethrough.

275. The device of claim 274, wherein said resistance layer comprises a polymer membrane with a oxygen-to-glucose permeability ratio of approximately 200:1.

276. The device of claim 272, wherein said interference layer comprises a hydrophobic membrane substantially permeable to hydrogen peroxide.

277. The device of claim 276, wherein said interference layer comprises a hydrophobic membrane substantially impermeable to chemical compositions having a molecular weight substantially greater than hydrogen peroxide.

278. The device of claim 272, wherein said electrolyte layer comprises a semipermeable hydrophilic coating.

279. The device of claim 278, wherein said electrolyte layer comprises a curable copolymer of a urethane polymer and a hydrophilic film-forming polymer.

280. The device of claim 272, wherein said enzyme layer contains glucose oxidase.

281. The device of claim 257, wherein said housing comprising said electronic circuit is filled with material comprising waxes and resins wherein said waxes and resins secure said electronic circuit within said housing.

282. The device of claim 257, wherein said electronic circuit operably connected to at least one of said electrodes is adapted for long-term operation.

283. The device of claim 257, wherein said housing further comprises an apparatus operatively connected to said electronic circuit for transmitting data to a location external to said device.

284. The device of claim 283, wherein said data transmitting apparatus comprises radiotelemetry.

285. The device of claim 284, wherein said device is wholly implantable.

286. The device of claim 285, wherein said device is sized and configured for being wholly implantable subcutaneously.

287. The device of claim 257, wherein said housing is substantially oval-shaped.

288. The device of claim 257, wherein said sensor further comprises a sensor interface dome that protrudes from said housing.

289. A device for measuring glucose in a tissue of a host comprising a wholly implantable device comprising a sensor comprising an interface tip for communicating with the tissue of said host, said tip comprising a fixation domain adapted for substantial fixation of said tip in a foreign body capsule, wherein said sensor tip fixation domain further comprises a capsular attachment layer made from surgical grade polyester velour on said sensor.

290. The device of claim 289, further comprising a securing element for securing said device to biological tissue.

291. The device of claim 290, wherein said securing element comprises one of polyester, polypropylene cloth, polytetrafluoroethylene felts and expanded polytetrafluoroethylene.

292. The device of claim 291, wherein said securing element comprises a polyester velour.

293. The device of claim 289, wherein said sensor tip fixation domain further comprises an angiogenic layer on said sensor.

294. The device of claim 293, wherein said angiogenic layer comprises one of hydrophilic polyvinylidene fluoride, mixed cellulose esters, polyvinyl chloride, polypropylene, polysulphone and polymethacrylate.

295. The device of claim 293, wherein said angiogenic layer comprises polytetrafluoroethylene.

296. The device of claim 289, further comprising a bioprotective membrane substantially impermeable to macrophages, said bioprotective membrane located proximal to said angiogenic layer.

297. The device of claim 296, wherein said bioprotective membrane comprises polytetrafluoroethylene.

298. The device of claim 296, wherein said bioprotective and angiogenic layers are formed from a polytetrafluoroethylene.

299. The device of claim 296, wherein said bioprotective membrane comprises pores having diameter ranging from about 0.1 micron to about 1.0 micron.

300. The device of claim 296, wherein said bioprotective membrane comprises pores having diameter ranging from about 0.2 micron to about 0.5 micron.

301. The device of claim 296, wherein said bioprotective membrane comprises one of polypropylene, polysulphone, polytetrafluoroethylene, and poly(ethylene terephthalate).

302. The device of claim 301, said sensor further comprising a membrane impregnated with an oxidase.

303. The device of claim 302, wherein said oxidase impregnated membrane comprises a resistance layer, and enzyme layer, an interference layer and an electrolyte layer.

304. The device of claim 302, wherein said oxidase impregnated membrane comprises a single homogeneous structure.

305. The device of claim 303, wherein said resistance layer restricts the transport of glucose therethrough.

306. The device of claim 303, wherein said resistance layer comprises a polymer membrane with a oxygen-to-glucose permeability ratio of approximately 200:1.

307. The device of claim 303, wherein said interference layer comprises a hydrophobic membrane substantially permeable to hydrogen peroxide.

308. The device of claim 307, said interference layer comprises a hydrophobic membrane substantially impermeable to chemical compositions having a molecular weight substantially greater than hydrogen peroxide.

309. The device of claim 303, wherein said electrolyte layer comprises a semipermeable hydrophilic coating.

310. The device of claim 309, wherein said electrolyte layer comprises a curable copolymer of a urethane polymer and a hydrophilic film-forming polymer.

311. The device of claim 303, wherein said enzyme layer contains glucose oxidase.

312. The device of claim 289, comprising a housing that has an electronic circuit and at least two electrodes operatively connected to said electronic circuit, wherein said sensor is operably connected to said electrodes of said housing.

313. The device of claim 312, wherein said housing comprising said electronic circuit is filled with material comprising waxes and resins wherein said waxes and resins secure said electronic circuit within said housing.

314. The device of claim 312 wherein said electronic circuit operably connected to at least one of said electrodes is adapted for long-term operation.

315. The device of claim 312, wherein said housing further comprises an apparatus operatively connected to said electronic circuit for transmitting data to a location external to said device.

316. The device of claim 315, wherein said data transmitting apparatus comprises radiotelemetry.

317. The device of claim 289, wherein said device is sized and configured for being wholly implantable subcutaneously.

318. The device of claim 289, wherein said housing is substantially oval-shaped.

319. The device of claim 289, wherein said sensor interface tip comprises a dome configuration.

320. The device of claim 289, wherein said sensor interface tip protrudes from said housing.

* * * * *

(12) EX PARTE REEXAMINATION CERTIFICATE (9332nd)
United States Patent
Shults et al.

(10) Number: US 6,741,877 C1
(45) Certificate Issued: *Oct. 4, 2012

(54) DEVICE AND METHOD FOR DETERMINING ANALYTE LEVELS

(75) Inventors: Mark C. Shults, Madison, WI (US); Stuart J. Updike, Madison, WI (US); Rathbun K. Rhodes, Madison, WI (US)

(73) Assignee: DexCom, Inc., San Diego, CA (US)

Reexamination Request:
No. 90/011,776, Jun. 29, 2011

Reexamination Certificate for:
Patent No.: 6,741,877
Issued: May 25, 2004
Appl. No.: 09/489,588
Filed: Jan. 21, 2000

( * ) Notice: This patent is subject to a terminal disclaimer.

Related U.S. Application Data

(60) Continuation of application No. 09/447,227, filed on Nov. 22, 1999, which is a division of application No. 08/811,473, filed on Mar. 4, 1997, now Pat. No. 6,001,067.

(51) Int. Cl.
*A61B 5/00* (2006.01)
*C12Q 1/00* (2006.01)

(52) U.S. Cl. ......... 600/345; 600/347; 600/365; 600/573

(58) Field of Classification Search ....................... None
See application file for complete search history.

(56) References Cited

To view the complete listing of prior art documents cited during the proceeding for Reexamination Control Number 90/011,776, please refer to the USPTO's public Patent Application Information Retrieval (PAIR) system under the Display References tab.

*Primary Examiner* — Jeanne M Clark

(57) ABSTRACT

Devices and methods for determining analyte levels are described. The devices and methods allow for the implantation of analyte-monitoring devices, such as glucose monitoring devices, that result in the delivery of a dependable flow of blood to deliver sample to the implanted device. The devices comprise a unique microarchitectural arrangement in the sensor region that allows accurate data to be obtained over long periods of time.

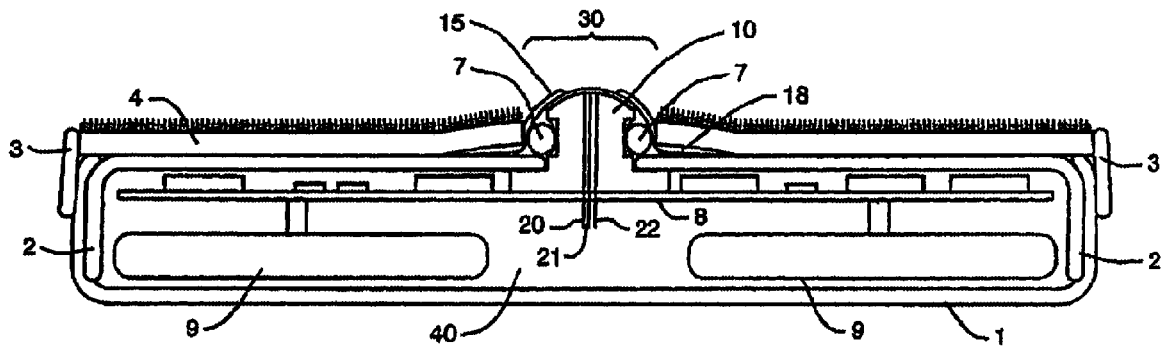

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 63-67, 161-164, 170, 172-176, 257-259 and 265-270 are cancelled.

New claims 321-344 are added and determined to be patentable.

Claims 1-62, 68-160, 165-169, 171, 177-256, 260-264 and 271-320 were not reexamined.

321. *A biological fluid measuring device, comprising:*
(a) *a housing comprising an electronic circuit and at least two electrodes operably connected to said electronic circuit, wherein at least one of the at least two electrodes is configured to generate a signal indicative of a glucose concentration of a host; and*
(b) *a sensor operably connected to said electrodes of said housing, said sensor comprising (i) a bioprotective membrane, and (ii) an angiogenic layer, said angiogenic layer positioned more distal to said housing than said bioprotective membrane, wherein said angiogenic layer comprises polytetrafluoroethylene, wherein said sensor further comprises a member for determining the amount of glucose in a biological sample, wherein said glucose determining member comprises a membrane containing glucose oxidase, said glucose oxidase-containing membrane positioned more proximal to said housing than said bioprotective membrane, wherein said glucose oxidase-containing membrane comprises a resistance layer, an enzyme layer, an interference layer and an electrolyte layer.*

322. *The device of claim 321, wherein said resistance layer restricts the transport of glucose therethrough.*

323. *The device of claim 321, wherein said resistance layer comprises a polymer membrane with an oxygen-to-glucose permeability ratio of approximately 200:1.*

324. *The device of claim 321, wherein said interference layer comprises a hydrophobic membrane substantially permeable to hydrogen peroxide.*

325. *The device of claim 324, wherein said interference layer comprises a hydrophobic membrane substantially impermeable to chemical compositions having a molecular weight substantially greater than hydrogen peroxide.*

326. *The device of claim 324, wherein said electrolyte layer comprises a semipermeable hydrophilic coating.*

327. *The device of claim 326, wherein said electrolyte layer comprises a curable copolymer of a urethane polymer and a hydrophilic film-forming polymer.*

328. *A device for measuring glucose in a biological fluid, comprising:*
a) *a housing comprising an electronic circuit and at least two electrodes operatively connected to said electronic circuit; and*
b) *a sensor operably connected to said electrodes of said housing, said sensor comprising an apparatus for determining the amount of glucose in a biological sample, said glucose determining apparatus operably associated with said electrodes and comprising a membrane impregnated with an oxidase, a bioprotective membrane substantially impermeable to macrophages, said bioprotective membrane positioned more distal to said housing than said oxidase impregnated membrane, and an angiogenic layer positioned more distal to said housing than said bioprotective membrane, wherein said oxidase impregnated membrane comprises a resistance layer, an enzyme layer, an interference layer and an electrolyte layer, wherein the sensor further comprises a sensor interface dome.*

329. *The device of claim 328, wherein said resistance layer restricts the transport of glucose therethrough.*

330. *The device of claim 328, wherein said resistance layer comprises a polymer membrane with an oxygen-to-glucose permeability ratio of approximately 200:1.*

331. *The device of claim 328, wherein said interference layer comprises a hydrophobic membrane substantially permeable to hydrogen peroxide.*

332. *The device of claim 328, wherein said interference layer comprises a hydrophobic membrane substantially impermeable to chemical compositions having a molecular weight substantially greater than hydrogen peroxide.*

333. *The device of claim 328, wherein said electrolyte layer comprises a semipermeable hydrophilic coating.*

334. *The device of claim 333, wherein said electrolyte layer comprises a curable copolymer of a urethane polymer and a hydrophilic film-forming polymer.*

335. *The device of claim 328, wherein said enzyme layer contains glucose oxidase.*

336. *A biological fluid measuring device, comprising:*
a) *a housing comprising an electronic circuit and at least two electrodes operably connected to said electronic circuit;*
b) *a sensor operably connected to said electrodes of said housing, said sensor comprising (i) a bioprotective membrane, and (ii) an angiogenic layer, said angiogenic layer positioned more distal to said housing than said bioprotective membrane, wherein said sensor further comprises a membrane for determining the amount of glucose in a biological sample, wherein said glucose determining membrane comprises glucose oxidase, wherein said glucose determining membrane comprises a resistance layer, an enzyme layer, an interference layer and an electrolyte layer; and*
c) *a member for securing said device to biological tissue, and securing member associated with said housing;*
*wherein the device is capable of exhibiting, at a glucose concentration of about 400 mg/dL, no more than a 10% drop in sensor output over a range of $pO_2$ from about 150 mm Hg down to about 30 mm Hg.*

337. *The device of claim 336, wherein said oxidase impregnated membrane comprises a single homogeneous structure.*

338. *The device of claim 336, wherein said resistance layer restricts the transport of glucose therethrough.*

339. *The device of claim 338, wherein said resistance layer comprises a polymer membrane with an oxygen-to-glucose permeability ratio of approximately 200:1.*

340. The device of claim 336, wherein said interference layer comprises a hydrophobic membrane substantially permeable to hydrogen peroxide.

341. The device of claim 340, wherein said interference layer comprises a hydrophobic membrane substantially impermeable to chemical compositions having a molecular weight substantially greater than hydrogen peroxide.

342. The device of claim 336, wherein said electrolyte layer comprises a semipermeable hydrophilic coating.

343. The device of claim 342, wherein said electrolyte layer comprises a curable copolymer of a urethane polymer and a hydrophilic film-forming polymer.

344. The device of claim 336, wherein said enzyme layer contains glucose oxidase.

\* \* \* \* \*